(12) United States Patent
Molmenti et al.

(10) Patent No.: US 11,844,513 B2
(45) Date of Patent: Dec. 19, 2023

(54) KNOT-TYING DEVICE FOR SURGICAL SUTURES

(71) Applicants: Ernesto Molmenti, Great Neck, NY (US); Alexia McCann, Tucson, AZ (US)

(72) Inventors: Ernesto Molmenti, Great Neck, NY (US); Alexia McCann, Tucson, AZ (US)

( * ) Notice: Subject to any disclaimer, the term of this patent is extended or adjusted under 35 U.S.C. 154(b) by 70 days.

(21) Appl. No.: 17/690,750

(22) Filed: Mar. 9, 2022

(65) Prior Publication Data

US 2022/0370063 A1 Nov. 24, 2022

Related U.S. Application Data

(63) Continuation of application No. 16/555,200, filed on Aug. 29, 2019, now Pat. No. 11,311,286.

(60) Provisional application No. 62/776,121, filed on Dec. 6, 2018, provisional application No. 62/732,656, filed on Sep. 18, 2018, provisional application No. 62/724,301, filed on Aug. 29, 2018.

(51) Int. Cl.
*A61B 17/04* (2006.01)
*A61B 17/00* (2006.01)

(52) U.S. Cl.
CPC ............... *A61B 17/0469* (2013.01); *A61B 2017/00398* (2013.01); *A61B 2017/00862* (2013.01); *A61B 2017/0474* (2013.01)

(58) Field of Classification Search
CPC ........ A61B 17/0469; A61B 2017/0474; A61B 2017/00398; A61B 2017/00862; A61B 2090/037; A61B 2017/00535; A61B 17/00491; A61B 2017/00336; A61B 2017/00349; A61B 2017/00477; A61B 2017/00876; A61B 17/0483
See application file for complete search history.

(56) References Cited

U.S. PATENT DOCUMENTS 5,447,512 A * 9/1995 Wilson .............. A61M 25/0041
606/139

* cited by examiner

*Primary Examiner* — Julian W Woo
(74) *Attorney, Agent, or Firm* — Amster Rothstein & Ebenstein LLP

(57) ABSTRACT

A knot tying device including a sheath configured for placement over a surgical instrument. The sheath includes a proximal end portion and a distal end portion. The distal end portion is elastically reconfigurable between a straightened configuration and a hook shaped configuration. Position of the sheath on the surgical instrument is adjustable between an extended position in which the sheath extends beyond a distal tip of the surgical instrument and a retracted position in which the sheath is pulled back from the distal tip of the surgical instrument. The distal end portion is in the hook shaped configuration when the sheath is in the extended position and the distal end portion is in the straightened configuration when the sheath is in the retracted position.

19 Claims, 28 Drawing Sheets

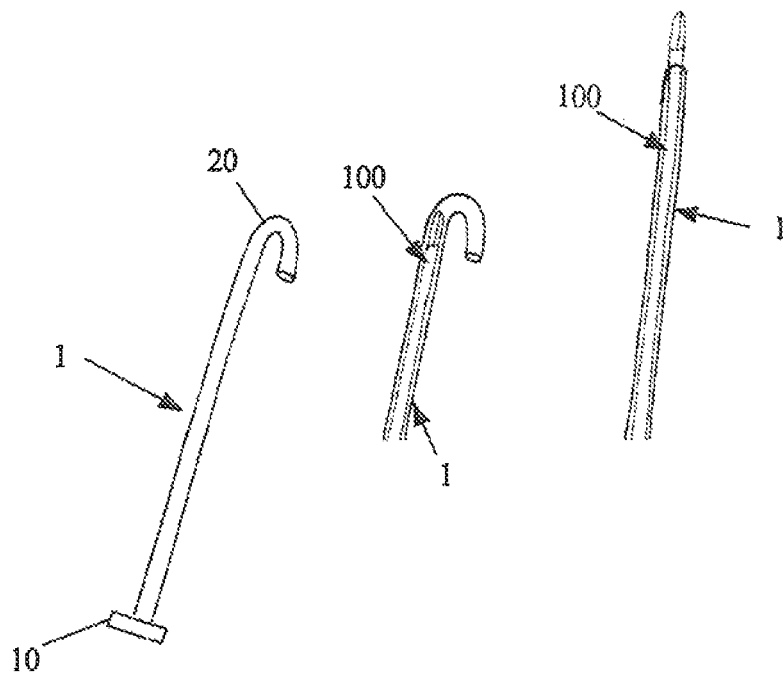
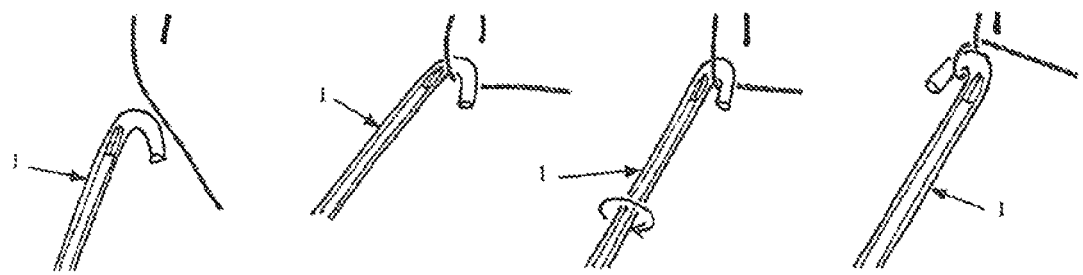
FIG. 1　　FIG. 2A　　FIG. 2B
FIG. 3A　　FIG. 3B　　FIG. 3C　　FIG. 3D

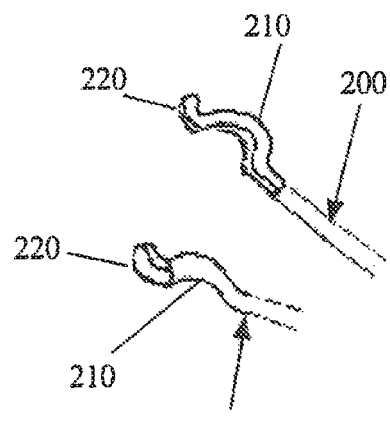
FIG. 14
FIG. 15
FIG. 16A
FIG. 16B
FIG. 16C
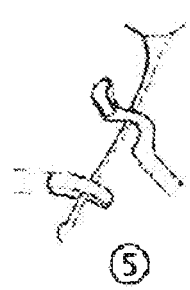
FIG. 16D
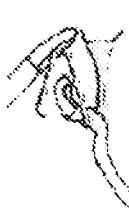
FIG. 16E
FIG. 16F
FIG. 16G
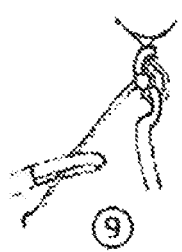
FIG. 16H
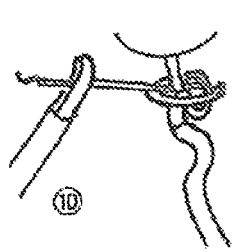
FIG. 16I
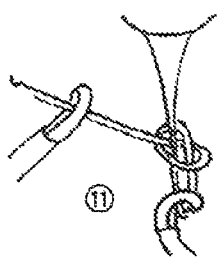
FIG. 16J
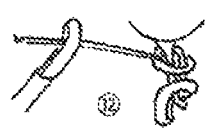
FIG. 16K

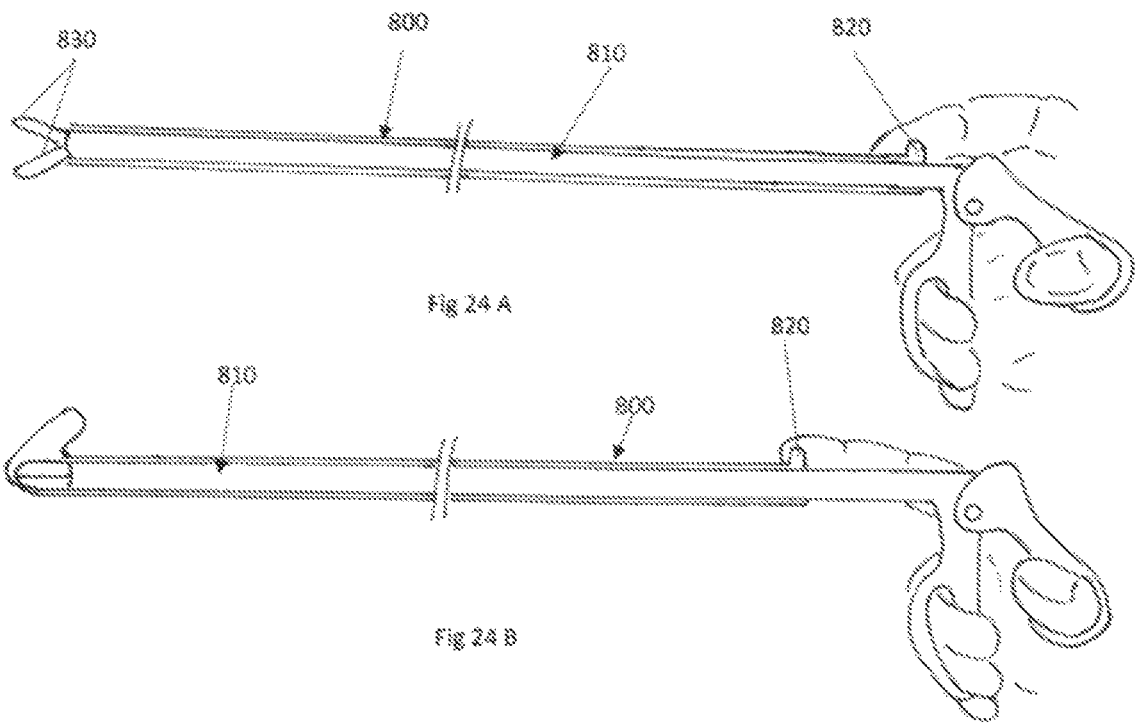

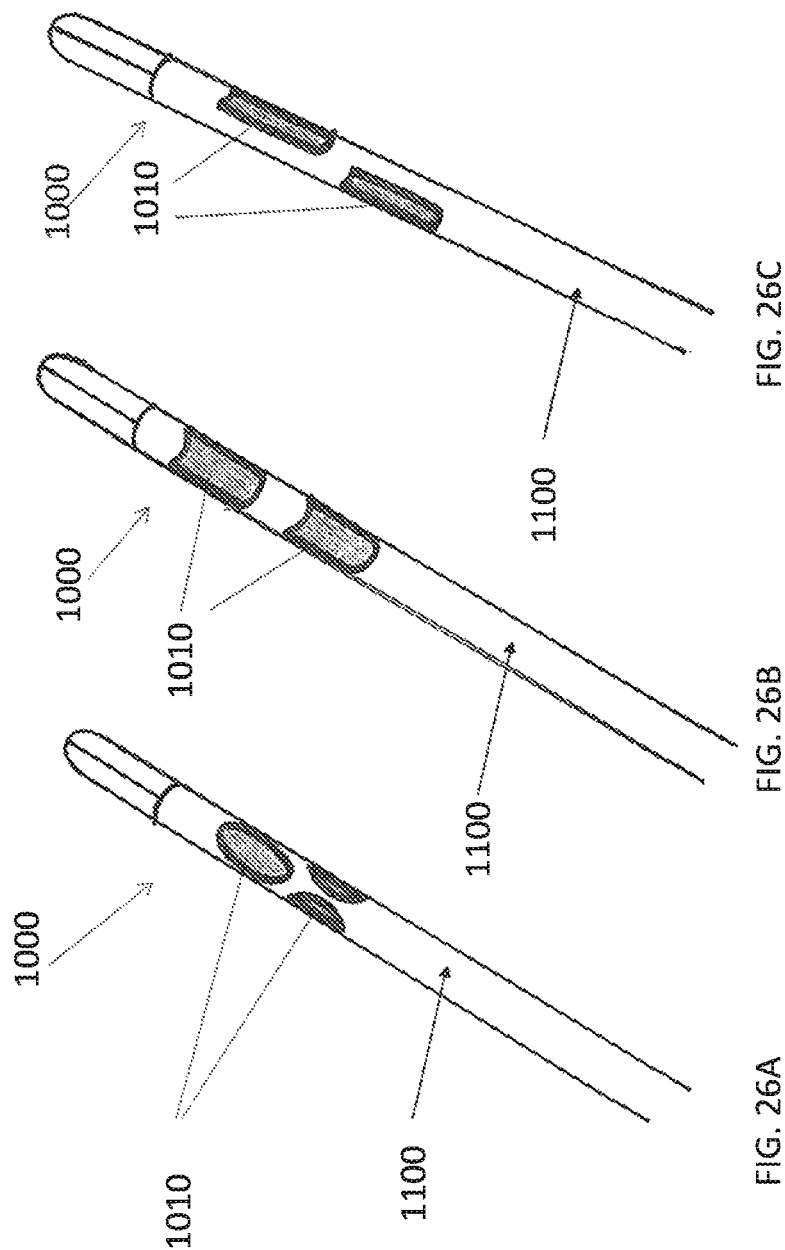

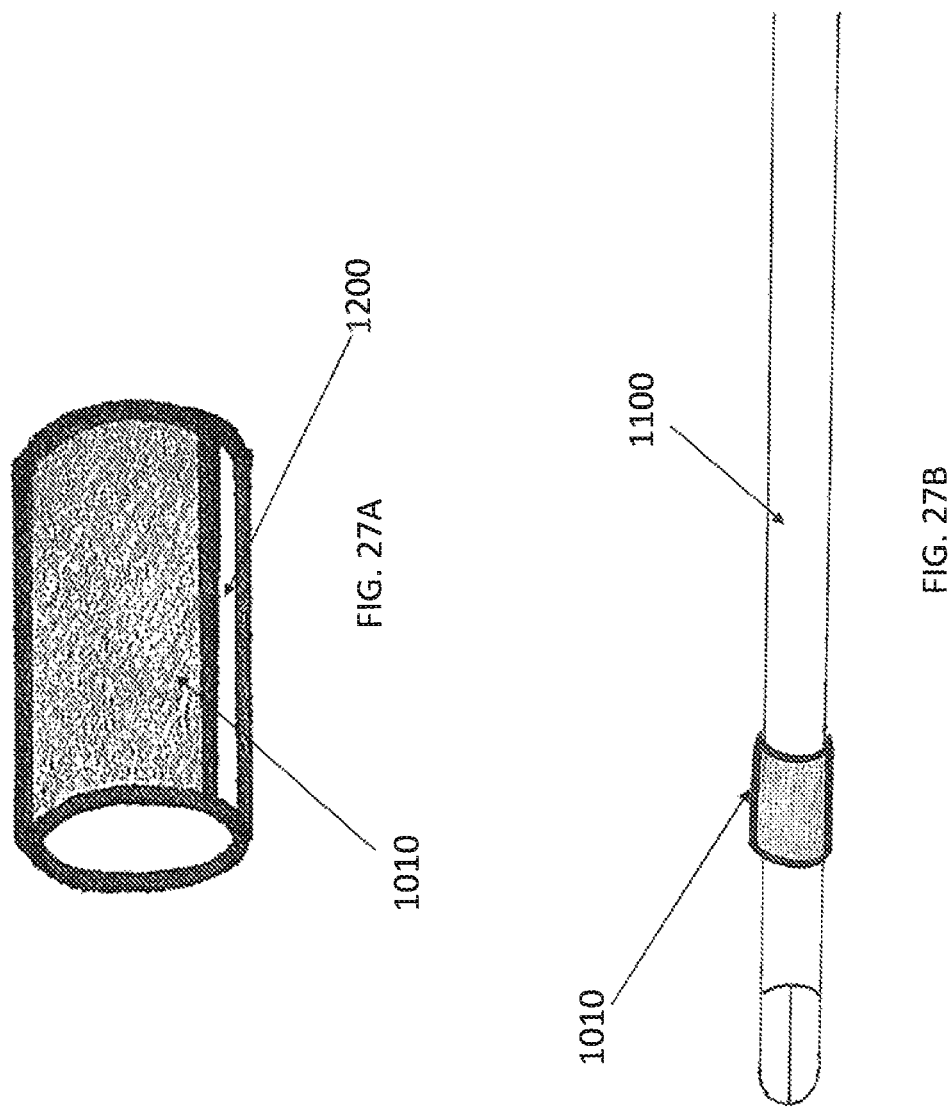

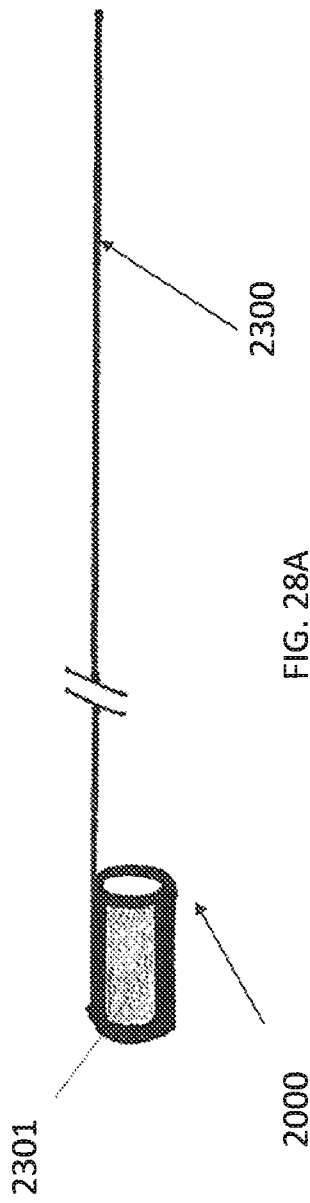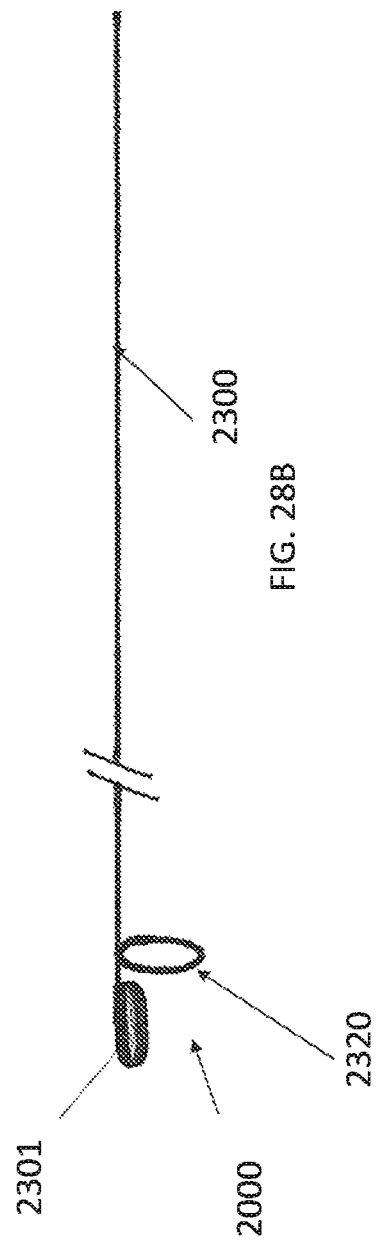

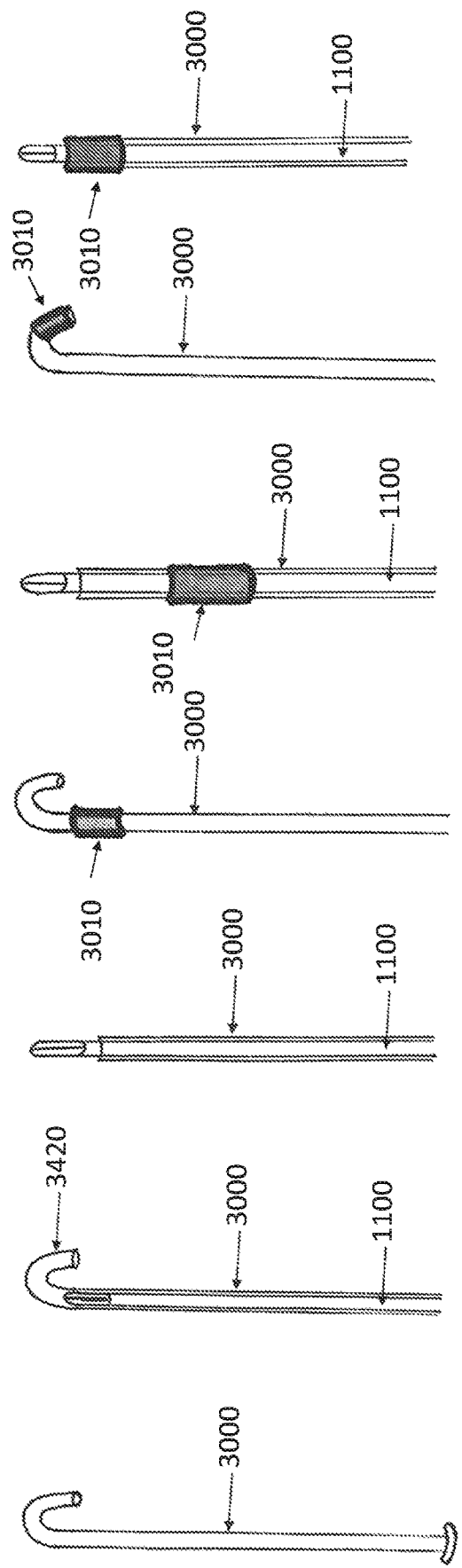

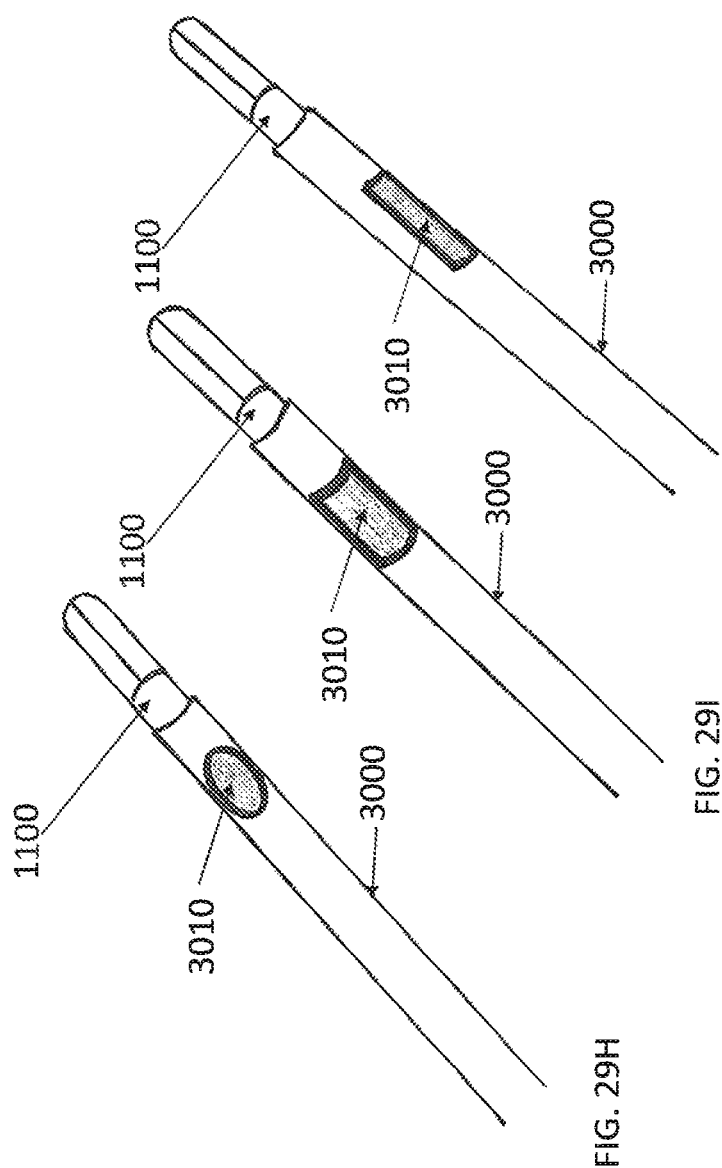

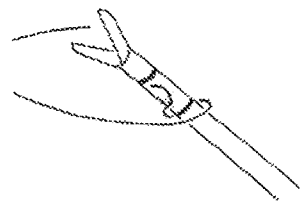
FIG. 30D
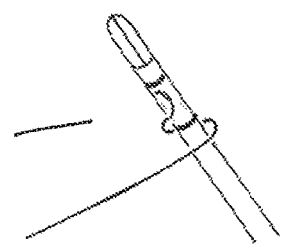
FIG. 30C
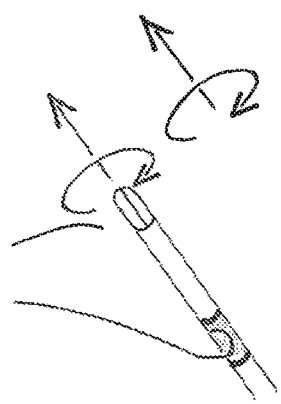
FIG. 30B
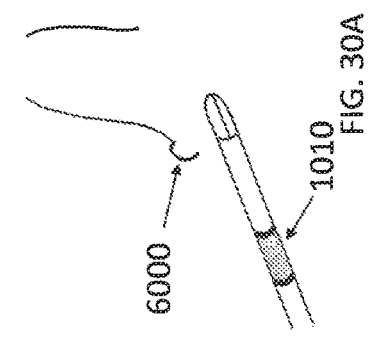
FIG. 30A
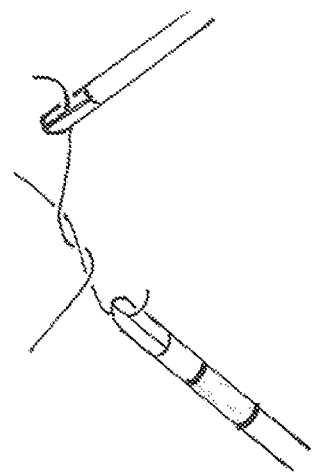
FIG. 30H
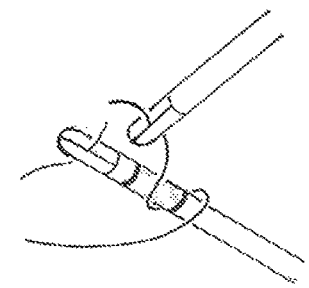
FIG. 30G
FIG. 30F
FIG. 30E
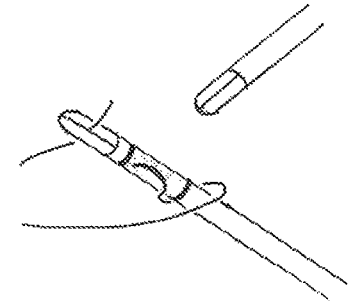

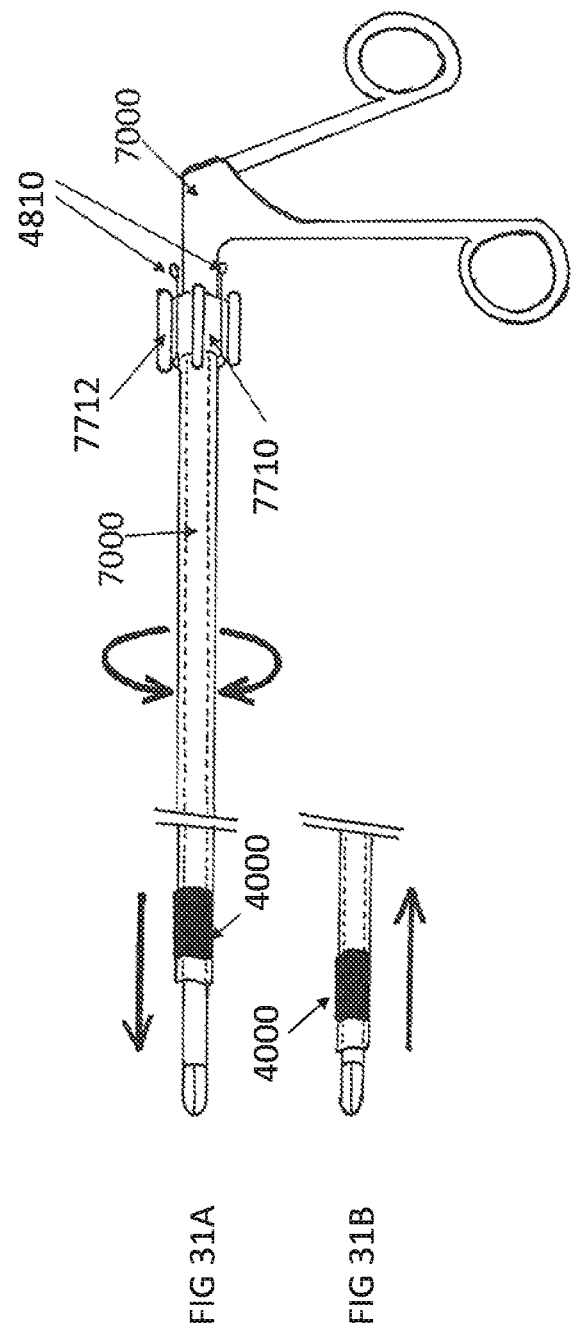

KNOT-TYING DEVICE FOR SURGICAL SUTURES

RELATED APPLICATION

This application is a continuation of U.S. patent application Ser. No. 16/555,200, filed Aug. 29, 2019, now U.S. Pat. No. 11,311,286, and entitled KNOT-TYING DEVICE FOR SURGICAL SUTURES, which in turn claims priority to and the benefit of U.S. Provisional Application No. 62/724,301, filed Aug. 29, 2018 and entitled KNOT-TYING DEVICE FOR SURGICAL SUTURES, U.S. Provisional Application No. 62/732,656, filed Sep. 18, 2018 and entitled KNOT-TYING DEVICE FOR SURGICAL SUTURES, and U.S. Provisional Application No. 62/776,121, filed Dec. 6, 2018 and entitled KNOT-TYING DEVICE FOR SURGICAL SUTURES, and the contents of these applications are incorporated herein by reference in their entirety.

FIELD OF THE INVENTION

The present invention relates generally to medical apparatus and methods, and more particularly, the present invention relates to methods, devices, and kits for tying knots in sutures used in surgical procedures.

BACKGROUND

Suturing and knot tying are difficult and time consuming steps in laparoscopic and robotic procedures. Knot tying techniques require significant experience due to the limited operating space and restricted movement. Such techniques typically involve the use of needle drivers, or needle holders, and other instruments to grasp and manipulate needles and sutures to enable free-hand suturing of wounds or surgical incisions within the body during laparoscopic, robotic and open procedures.

The conventional knot tying techniques increase the length of time of the overall procedure, cause strain and fatigue to the surgeon, limit the procedures that can be performed by clinicians with limited experience, limited skill or in the training stages of their careers, and may result in postoperative patient complications.

Accordingly, there is a need for improved knot tying devices in minimally invasive procedures, such as laparoscopic and robotic procedures.

SUMMARY OF THE INVENTION

An object of the present invention is to provide a knot tying device that allows for less challenging and simpler knot tying techniques as compared to currently known techniques that involve the use of conventional laparoscopic and robotic instruments (such as needle drivers).

A knot tying device according to an exemplary embodiment of the invention comprises: a sheath configured for placement over a surgical instrument, the sheath comprising: a proximal end portion; a distal end portion having a first configuration in which the distal end portion is straight and a second configuration in which the distal end portion has a hook shape (of variable, adjustable or fixed angulation), wherein the distal end portion is in the second configuration when the distal end portion extends beyond a distal end portion of the surgical instrument.

A knot tying device assembly according to an exemplary embodiment of the present invention comprises: a surgical instrument; and a knot tying device, the knot tying device comprising: a sheath disposed over the surgical instrument, the sheath comprising: a proximal end portion; and a distal end portion that is elastically reconfigurable between a straightened configuration and a hook shaped configuration, wherein position of the sheath on the surgical instrument is adjustable between an extended position in which the sheath extends beyond a distal tip of the surgical instrument and a retracted position in which the sheath is pulled back from the distal tip of the surgical instrument, and wherein the distal end portion is in the hook shaped configuration when the sheath is in the extended position and the distal end portion is in the straightened configuration when the sheath is in the retracted position.

In an exemplary embodiment, the surgical instrument is a laparoscopic surgical instrument.

In an exemplary embodiment, the surgical instrument is of a type selected from the group consisting of: cannulas, trocars, scissors, graspers, forceps, hooks, probes, knot pushers, dissectors of all types, needles, needle holders, needle drivers, rigid scopes, trocar incision closure devices, catheters, harmonic scalpels, vessel sealing devices (e.g., Ligasure™), energy delivery devices (e.g., Thunderbeat™), irrigators, suctions, electric/hydraulic/pneumatic/sonic devices, and retractors.

In an exemplary embodiment, at least a portion of the sheath is made of an elastic material or a material that has a configuration or design that allows for a stretch/bend/angulation to occur.

In an exemplary embodiment, the sheath is made of a material selected from the group consisting of: metal, magnetic or electromagnetic material, polyethylene, silicone rubber, natural rubber, PVC, polyurethane, polypropylene, polyester, polyether ether ketone, polyphenylsulfone, nylon, polytetrafluoroethylene, resin and combinations thereof. It should be appreciated that the materials are not limited to those listed herein, and other types of materials may be used to form the knot tying device.

In an exemplary embodiment, the knot tying device further comprises an activation mechanism that moves the sheath with at least one of linear or rotational movement relative to the surgical instrument. The activation mechanism may also allow for adjustment to the diameter or length of the sheath or knot tying device.

In an exemplary embodiment, the activation mechanism is of a type selected from but not limited to the group consisting of: hydraulic, pneumatic, ultrasonic, sonic, mechanical, electrical, magnetic, and combinations thereof.

A knot tying device according to an exemplary embodiment of the invention comprises: a magnet that is an integral or removable part of a surgical instrument. Alternatively, the magnet is part of a sheath configured for placement over a surgical instrument. The sheath, containing one or more magnets, could be of variable length and shape. The sheath could be fixed relative to the surgical instrument or movable along the length and/or the circumference of the surgical instrument.

In exemplary embodiments, the sheath may include a proximal end portion and a distal end portion, and the one or more magnets may be disposed at one or both of the proximal and distal end portions and/or at any other position along the shaft. The one or more magnets are configured to allow for one or more needles to adhere to it. The one or more magnets may include permanent or removable/attachable/detachable magnets or electromagnets, for example.

A knot tying device assembly according to an exemplary embodiment of the present invention comprises: a surgical instrument with an integral (or attachable/removable) magnetic element. The knot tying device may comprise a sheath disposed over the surgical instrument. The knot tying device may comprise a proximal end portion and a distal end portion, and one or more magnets may be disposed at one or both of the proximal and distal end portions and/or at other locations along the knot tying device.

The sheath may have a shape that is static (for example, a fixed straight shape). Alternatively, the sheath may have a shape that is reconfigurable between a straightened configuration and a hook, coiled, or other non-straight configuration. The position of the sheath on the surgical instrument may be fixed or adjustable. If adjustable, the adjustable motion may encompass linear and/or rotational motions. Furthermore, the length and/or diameter of the knot tying device and/or its sheath may be fixed or adjustable. The sheath may also have a fixed position or an extended position in which a curved/coiled/non-straight portion of the sheath extends beyond a distal tip of the surgical instrument and a retracted position in which the sheath is pulled back from the distal tip of the surgical instrument, and wherein the distal end portion is in the hook/coiled/other shaped configuration when the sheath is in the extended position and the distal end portion is in the straightened configuration when the sheath is in the retracted position.

In exemplary embodiments, the instrument itself may contain one or more magnets that could be fixed in place or placed at will without the need of a sheath around the instrument.

These and other features and advantages of the present invention will be presented in more detail in the following detailed description and the accompanying figures which illustrate by way of example principles of the invention.

DESCRIPTION OF THE DRAWINGS

Various exemplary embodiments of this invention will be described in detail, with reference to the following figures, wherein:

FIG. 1 is a perspective view of a knot tying device according to an exemplary embodiment of the present invention;

FIGS. 2A and 2B are perspective views of a knot tying device according to an exemplary embodiment of the present invention disposed on a surgical instrument;

FIGS. 3A-3F show a knot tying procedure using the knot tying device according to an exemplary embodiment of the present invention;

FIG. 14 is a partial perspective view of a knot tying device according an exemplary embodiment of the present invention;

FIG. 15 is a partial perspective view of a knot tying device according an exemplary embodiment of the present invention;

FIGS. 16A-16K show a knot tying procedure using a knot tying device according to an exemplary embodiment of the present invention;

FIGS. 24A and 24B illustrate a knot tying device according to an exemplary embodiment of the present invention where the knot tying device is built into a laparoscopic surgical instrument so that the knot tying device and the surgical instrument form a unitary structure;

FIGS. 26A-26C are perspective views of a knot tying device according to an exemplary embodiment of the present invention;

FIGS. 27A and 27B are perspective views of a knot tying device according to an exemplary embodiment of the present invention;

FIGS. 28A and 28B are perspective views of a knot tying device according to an exemplary embodiment of the present invention;

FIGS. 29A-29J are perspective views of a knot tying device according to an exemplary embodiment of the present invention disposed on a surgical instrument;

FIGS. 30A-30H illustrate a knot tying procedure using the knot tying device according to an exemplary embodiment of the present invention;

FIGS. 31A-31B are perspective views of a knot tying device according to an exemplary embodiment of the present invention.

DETAILED DESCRIPTION

Figures 3E, 3F:
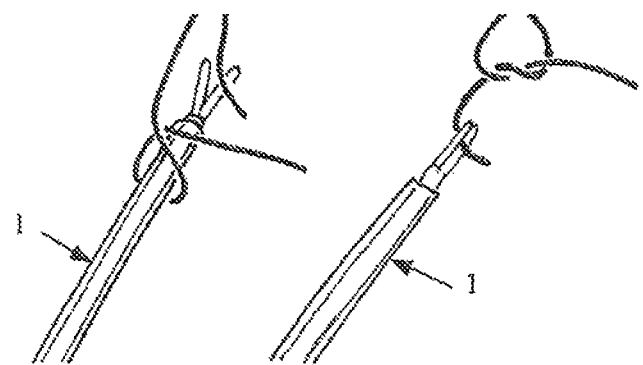

For the purposes of the present description, the term "proximal" is intended to mean at a position closest to the clinician during a procedure (and furthest from the patient) and/or relates to a portion of an apparatus that is used to control operation and/or movement of the apparatus and the term "distal" is intended to mean at a position furthest from the clinician (and closest to the patient) and/or relates to a portion of an apparatus that is intended for insertion into a surgical site of a patient for performance of a surgical procedure.

A knot tying device according to an exemplary embodiment of the present invention is made up of a sheath that can be placed over any laparoscopic instrument (such as graspers, needle drivers, dissectors, etc.). Although the description herein is provided in the context of laparoscopy, it should be appreciated that the inventive knot tying device may be suitable for use with other types of procedures, such as, for example, robotic surgery, telesurgery, battlefield procedures, interventional radiology and veterinary medicine.

In exemplary embodiments, the inventive knot tying device may have the following characteristics:
- Can be potentially rotated to and fro, and both clockwise and counter-clockwise (based on the needs of the user);
- Can be potentially be enlarged or decreased in diameter and/or length.
- Can be used safely in training programs;
- Allows surgeons with minimal or no experience in knot-tying to achieve successful results;
- Allows the operator to tie knots without having to change or even withdraw the instruments being used in the procedure;
- Allows the operator to have a knot-tying device on as many instruments as desired during the case, allowing for the use of any instrument when tying knots;
- Can be adapted to any instruments, avoiding the need to purchase new instruments or to alter current surgical trays;
- Is simple, cheap, disposable, and can be placed on the desired instruments throughout the entire case without causing any interference with the procedure;
- The distal end of the device could have a bend whose curvature can be overcome by sliding the instrument that is being placed within it (similar to a drinking straw being straightened);

In exemplary embodiments, the knot tying device may be activated to have linear motion to allow for back and forth motion on the surgical instrument, and/or rotational motion (clockwise/counter-clockwise) to allow for the device to rotate and create a knot. The linear and rotational motions may be independent of and/or dependent on one another.

Alternatively, the device may have only a linear motion relative to the surgical instrument, and the rotation may be achieved by rotating the entire instrument.

Alternatively, the device may have only rotational motion relative to the surgical instrument, and the linear motion may be achieved by rotating the entire instrument.

Alternatively, the device may allow for its diameter and/or length to be expanded or decreased, simultaneously and/or independently of each other.

In exemplary embodiments, the knot tying device may be deployed/activated manually and/or through the use of mechanical, hydraulic, pneumatic, sonic, ultrasonic, electronic, magnetic/electromagnetic components, or combinations thereof. It should be appreciated that the deployment/activation mechanism is not limited to the types listed herein.

In exemplary embodiments, the knot tying device (either with or without a sheath) can be placed on needle-drivers, graspers, or any other laparoscopic/robotic instrument used during a procedure. Knot tying devices of various diameters, sizes, shapes, and configurations can be used to adapt to a variety of instruments of various shapes and/or sizes. Furthermore, the diameter and/or length of a knot tying device may be adjusted to fit into various instruments of various lengths and diameters.

Although the knot tying device described herein has various outlines, it should be appreciated that it may have various other shape profiles to adapt to the clinician's preference, size of the operative field and/or characteristics of the suture being used. For example, the knot tying device may have one or more bends, angulations, curls, spirals and/or coils.

In exemplary embodiments, the knot tying device may be placed over multiple instruments being used simultaneously. This allows the clinician to tie knots with any of the instruments being used in the procedure.

In exemplary embodiments, the knot tying device may include radio-opaque elements or may be entirely radio-opaque.

In exemplary embodiments, the knot tying device may be or have parts that are transparent or made of different colors (radio-opaque or not) or otherwise labeled to help identify sizes and specific uses.

In exemplary embodiments, the knot tying device may be made available in a variety of sizes so that an appropriate size may be selected depending on the type of procedure, such as, for example, adult cases, pediatric cases and/or interventional radiology cases.

In exemplary embodiments, the knot tying device may be used in a purely percutaneous manner. In this regard, the knot tying device may be introduced by directly puncturing the skin, with no trocar needed, by placing the device on a very thin instrument or a needle. This would be appropriate, for example, when the clinician has both instruments otherwise engaged and wishes to tie a knot.

In exemplary embodiments, the knot tying device may not be apparent when viewing the instrument, and can be located within the body of the instrument itself.

In exemplary embodiments, the knot tying device may be associated with luminescent, incandescent, light, or other type of markers and/or sensors (such as pressure, temperature, pH, tension) and/or imaging modalities (such as ultrasound or other imaging modalities).

FIG. 1 shows a knot-tying device, generally designated by reference number 1, according to an exemplary embodiment of the present invention. The knot-tying device 1 is an elongated sheath having a proximal end portion 10 and a distal end portion 20. The knot-tying device 1 is preferably a unitary structure and may be made of elastic polymeric material, such as, for example, polyethylene, silicone rubber, natural rubber, PVC, polyurethane, polypropylene, polyester, polyether ether ketone, polyphenylsulfone, nylon, and polytetrafluoroethylene (e.g., Teflon). The material is preferably strong and durable enough to withstand the rigors of laparoscopic procedures while maintaining its general shape profile, flexible enough to perform effectively during use and delicate enough to avoid injury to surrounding structures it may come in contact with during use. Portions of the knot tying device 1 may be made of different materials to provide variations in properties along the length of the device, for example, variations in flexibility along the length of the device. In this regard, proximal portions of the knot tying device may not need to be as flexible as distal portions of the device.

In an exemplary embodiment, the knot tying device 1 is made using a molding process, resulting in the distal end portion 20 of the knot tying device 1 taking on a hook or bent shape. Due to the flexible nature of the material, the knot tying device 1 is able to elastically deform. For example, as shown in FIG. 2A, the knot tying device 1 may be flexed over a surgical instrument 100 so that the surgical instrument 100 is essentially sheathed within the knot tying device 1 with the hook shaped distal end portion 20 of the knot tying device 1 extending beyond the distal end portion of the surgical instrument 100. As explained below, the knot tying device 1 in this configuration is now available for tying of surgical sutures. As shown in FIG. 2B, the knot tying device 1 may be pulled back in the proximal direction over the surgical instrument 100 so that the tool end of the surgical instrument 100 is exposed for use. In this configuration, the distal end portion 20 of the knot tying device 1 is elastically deformed into a straightened shape.

In exemplary embodiments, the sheath that makes up the knot tying device 1 can be placed over needle-drivers, graspers, or any other laparoscopic instrument used during a procedure. Sheaths of various diameters can be used to adapt to the desired instruments. Although the knot tying device 1 is described herein as having a bent or hook shape, it should be appreciated that the knot tying device may have various other shape profiles to adapt to the clinician's preference, size of the operative field and/or characteristics of the suture being used. For example, the knot tying device 1 may have one or more bends, angulations, curls, spirals and/or coils.

In exemplary embodiment, sheaths may be placed over multiple instruments being used simultaneously. This allows the clinician to tie knots with any of the instruments being used in the procedure.

In exemplary embodiments, the knot tying device 1 may include radio-opaque elements or may be entirely radio-opaque.

In exemplary embodiments, the knot tying device 1 may be transparent or made of different colors (radio-opaque or not) or otherwise labeled to help identify sizes and specific uses.

In exemplary embodiments, the knot tying device 1 may be made available in a variety of sizes so that an appropriate size may be selected depending on the type of procedure, such as, for example, adult cases, pediatric cases and/or interventional radiology cases.

In exemplary embodiments, the knot tying device 1 may be used in a purely percutaneous manner. In this regard, the knot tying device 1 may be introduced by directly puncturing the skin, with no trocar needed, by placing the device on a very thin instrument or a needle. This would be appropriate, for example, when the clinician has both instruments otherwise engaged and wishes to tie a knot.

FIGS. 3A-3F show a knot tying procedure using the knot tying device 1 according to an exemplary embodiment of the invention. In FIG. 3A, after the suture is placed, the ends to be tied are addressed. At this point, the knot tying device 1 has been pushed forward in the distal direction relative to the surgical instrument 100 or, alternatively the surgical instrument 100 has been pulled back in the proximal direction relative to the knot tying device 1, so that the hook shaped distal end portion 20 of the knot tying device 1 is made available for the knot tying procedure. As shown in FIG. 3B, the clinician first uses the knot tying device 1 to hook one of the suture ends. Then, as shown in FIGS. 3C and 3D, the knot tying device 1 is rotated (clockwise in this example) and turned circumferentially, thereby creating at least one loop in the end of the suture. Alternatively, the suture can be looped one or more times around the hooked end of the knot tying device 1 with no need to rotate the knot tying device 1. At this point, the surgical instrument 100 is pushed forward in the distal direction until the tool end of the instrument is exposed for use (or the knot tying device 1 is pulled back in the proximal direction), resulting in straightening of the hook shaped distal end portion 20 of the knot tying device 1. Then, as shown in FIG. 3E, the surgical instrument 1 is used to grasp the other end of the suture and, as shown in FIG. 3F, the knot is built and subsequently tied.

In exemplary embodiments, the knot tying device 1 may be single-use (disposable) or reusable. In exemplary embodiments in which the knot tying device 1 is made up of more than one component, each component may be interchangeable with a corresponding component on another knot tying device or may be intended for only a particular knot tying device (such as a specific size or type of knot tying device).

In exemplary embodiments, the knot tying device 1 may be moved manually and/or actuated in a variety of ways, using one or more of the following types of mechanisms:

Hydraulic/pneumatic (compressed fluid/gas)
  a. Hand pump
  b. Foot pump
  c. Electric pump
    i. Battery-operated
    ii. Plug in (e.g., line voltage, transformer, etc.)
  d. Mechanical kinetic/potential energy pump
Cog wheel mechanism (e.g., hand-drill with two cogwheels and a rotating arm)
Rack and pinion
Torque
Spiral/ratchet screwdriver mechanism
Zipper
Electric
  a. Battery-operated
  b. Plug in (e.g., line voltage, transformer, etc.)
Elastic band—kinetic/potential energy
Coil—kinetic/potential energy, finger activated
Motor/engine
  a. Individual
  b. Interchangeable
  c. Re-usable
    i. Individual
    ii. Interchangeable Ball point pen/click pen mechanism
Ultrasonic/sonic
Automated drive
   a. With safety measures such as, for example, pressure sensors, alert mechanisms, and/or automatic shut-off upon reaching a predetermined limit.
Trigger mechanism In exemplary embodiments, movement may be restricted to advance a specific distance (e.g., 1 cm, 2 cm, 5 cm) and to rotate a specific number of degrees (e.g., 45°, 90°, 180°, etc.) based on need. The parameters may be pre-set/fixed in advance or adjustable at will by the clinician (e.g., pre-set ratchet mechanism, pre-set scale, adjusting button/dial, etc.), either in advance or as needed during the procedure (based on tissues being sutured, type of suture being used, ability of the operator, and other factors).

FIGS. 4A, 4B, 5, 6, 7, 8, 9, 10, 11, 12 and 13 show various activation mechanisms and modifications that may be implemented so that the knot tying device 1 may be triggered, rotated or otherwise manipulated to complete a knot tying procedure.

Figure 4A:
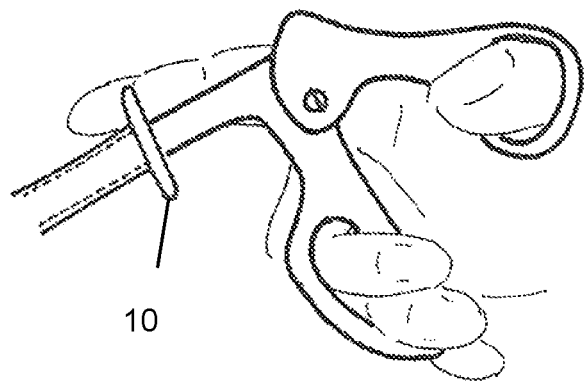
FIG. 4A illustrates an activation mechanism of a knot tying device according to an exemplary embodiment of the present invention.
Figure 4B:
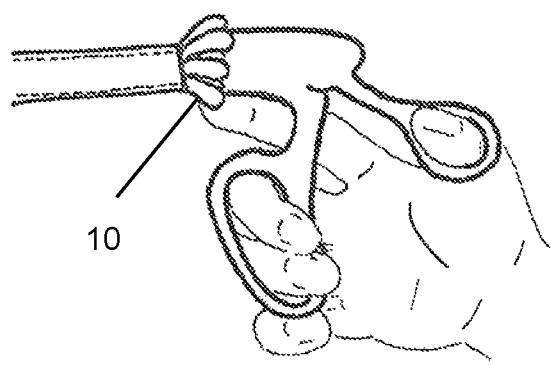
FIG. 4B illustrates an activation mechanism of a knot tying device according to an exemplary embodiment of the present invention.

As shown in FIGS. 4A and 4B, the knot tying device may be moved longitudinally and/or circularly with a finger while operating the instrument being used. In this regard, the proximal end portion 10 of the knot tying device 1 may include a flange or one or more protruding elements that can be engaged by a finger/thumb of the clinician to manipulate the knot tying device 1.

Figure 5:
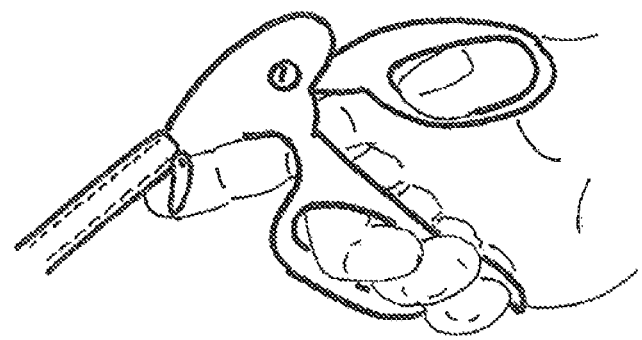
FIG. 5 illustrates an activation mechanism of a knot tying device according to an exemplary embodiment of the present invention.
Figure 6:
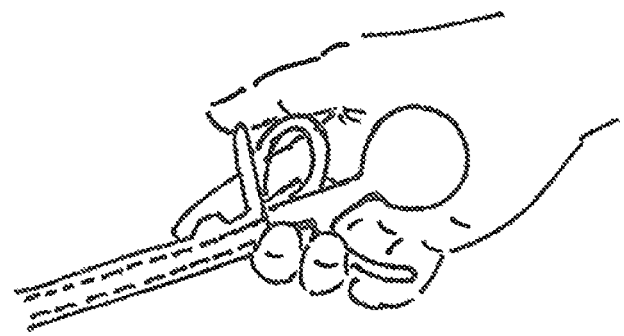
FIG. 6 illustrates an activation mechanism of a knot tying device according to an exemplary embodiment of the present invention.
Figure 7:
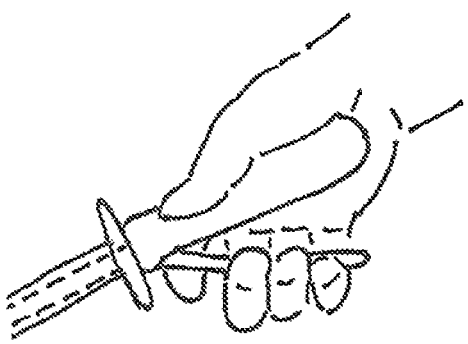
FIG. 7 illustrates an activation mechanism of a knot tying device according to an exemplary embodiment of the present invention.

FIG. 5 shows a trigger type of mechanism that may be engaged by the clinician's finger/thumb to manipulate the knot tying device 1. Such a trigger mechanism may be similar to those found in firearms.

Figure 8:
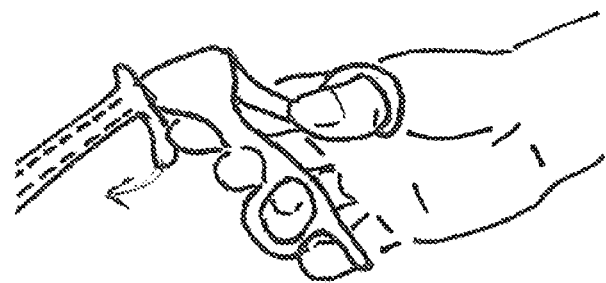
FIG. 8 illustrates an activation mechanism of a knot tying device according to an exemplary embodiment of the present invention.
Figure 9:
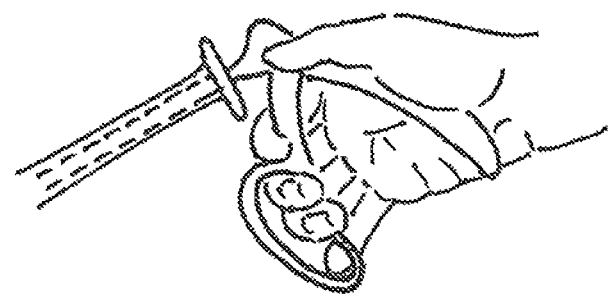
FIG. 9 illustrates an activation mechanism of a knot tying device according to an exemplary embodiment of the present invention.

FIGS. 6-9 show how the proximal end of the knot tying device 1 may be modified for use with various types of instruments having different types of handles. FIG. 8 in particular depicts the use of a trigger mechanism activated by a pushing rather than a pulling action.

Figure 10:
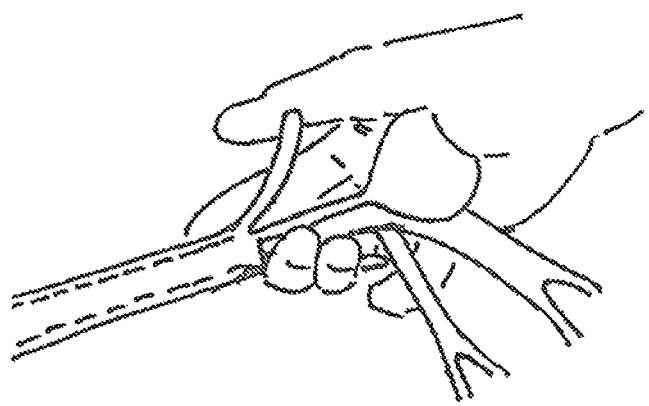
FIG. 10 illustrates an activation mechanism of a knot tying device according to an exemplary embodiment of the present invention.

A hand activated hydraulic/pneumatic (fluid/gas) mechanism is shown in FIG. 10, where the clinician presses with the hand on the reservoir. An additional lever is also included as a potential hybrid mechanism.

Figure 11:
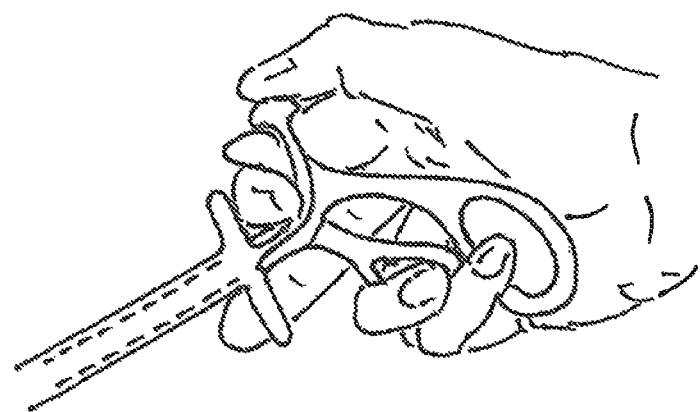
FIG. 11 illustrates an activation mechanism of a knot tying device according to an exemplary embodiment of the present invention.

A variation of the mechanism shown in FIG. 10 is shown in FIG. 11. While the thumb activates a hydraulic process, the middle finger (and potentially also the index finger) controls a manual mechanism (or some other type of mechanism).

Figure 12:
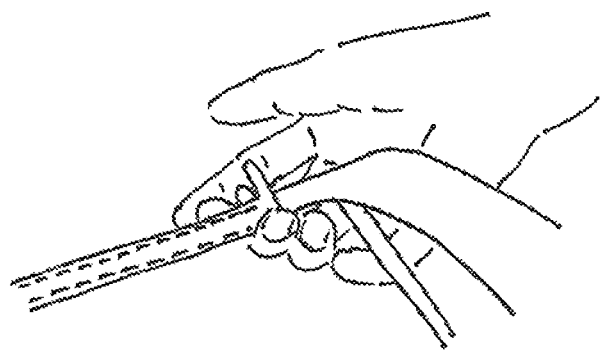
FIG. 12 illustrates an activation mechanism of a knot tying device according to an exemplary embodiment of the present invention.

Alternatively, as shown in FIG. 12, with a power source attached, the device may have two buttons to control longitudinal and circular movements of the sheath.

In exemplary embodiments, a mechanism similar to joysticks and computer gaming may be used.

In exemplary embodiments, the mechanism may be foot activated (such as with a pedal) or remotely activated (such as with a console), particularly if the device is used in robotic surgery.

Figure 13:
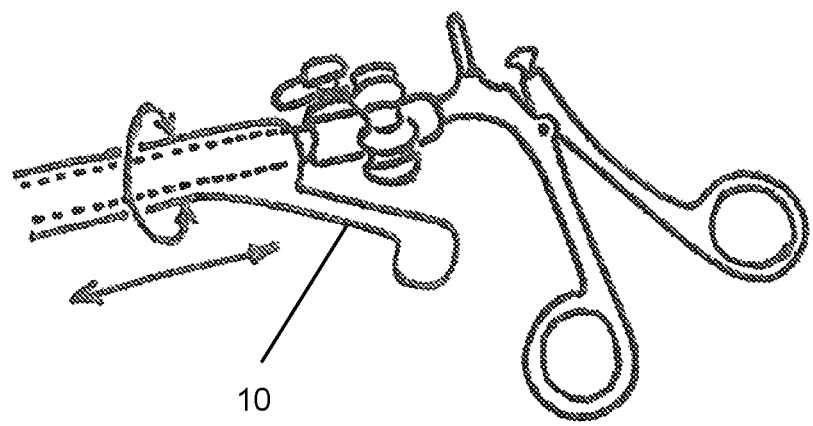
FIG. 13 illustrates an activation mechanism of a knot tying device according to an exemplary embodiment of the present invention.

FIG. 13 shows a variation of the knot tying device in which the proximal end portion 20 includes a single handle (or possibly more than one handle) to rotate and move the device back and forth. This allows the clinician to operate all of the controls of the instrument without interference from the knot tying device. This would be particularly useful in instances where the laparoscopic instrument has a cable, cord, rotating device, suction port or any other element located between the clinician's hand and the knot tying device 1.

In exemplary embodiments, the knot tying device may be made available as part of a kit. For example, the kit may contain one or more knot tying devices having a common size and type or varying sizes and types. The kit may contain additional elements, such as, for example, other types of surgical instruments and an instruction manual. In exemplary embodiments, the knot tying device may be single-use/disposable, while in other embodiments the knot tying device may be reusable. For example, the knot tying device may be sterilized after each use, using any of a variety of sterilization techniques, including, for example, steam under pressure (autoclaving), gamma radiation, dry heat or heat/chemical vapor. Components of the knot-tying device (such as the power supply, electric cables, foot pedal, console, motor, etc.) may also be single use or reusable, and for individual use or interchangeable.

FIG. 14 shows a distal end portion of a knot tying device, generally designated by reference number 200, according to another exemplary embodiment of the present invention. The distal end portion of the knot tying device 200 includes a first arcuate portion 210 and a second arcuate portion 220 that bends in a direction opposite to that of the first arcuate portion 210. The second arcuate portion 220 forms the distal tip of the knot tying device 200. The first arcuate portion 210 is positioned between the second arcuate portion 220 and proximal end portion of the knot tying device 200. The distal end portion of the knot tying device 200, including the first and second arcuate portions 210, 220, are formed by a pair of blades that may be open and closed in a scissor-like manner. In another exemplary embodiment, as shown in FIG. 15, only the second arcuate portion 220 that forms the distal tip of the knot tying device 200 includes a pair of blades that may be open and closed, with the first arcuate portion 220 merely being an extension of the solid handle of the knot tying device 200.

FIGS. 16A-16K show a knot tying procedure using the knot tying device 200 according to an exemplary embodiment of the invention. As shown in FIGS. 16A-16F, both ends of the suture are first brought together using, for example, a needle driver, and then the two ends are looped around the first arcuate portion 210. Then, as shown in FIGS. 16G and 16H, the second arcuate portion 220 is used to grasp the two suture ends close to the structure being tied. As shown in FIGS. 16I-16K, the knot can then be formed and tightened by manipulation of the needle driver and the knot tying device 200. As shown in FIG. 16K, the knot can be further tightened by sliding both ends along the opened (or alternatively, closed) blades of the second arcuate portion 220.

Figure 17:
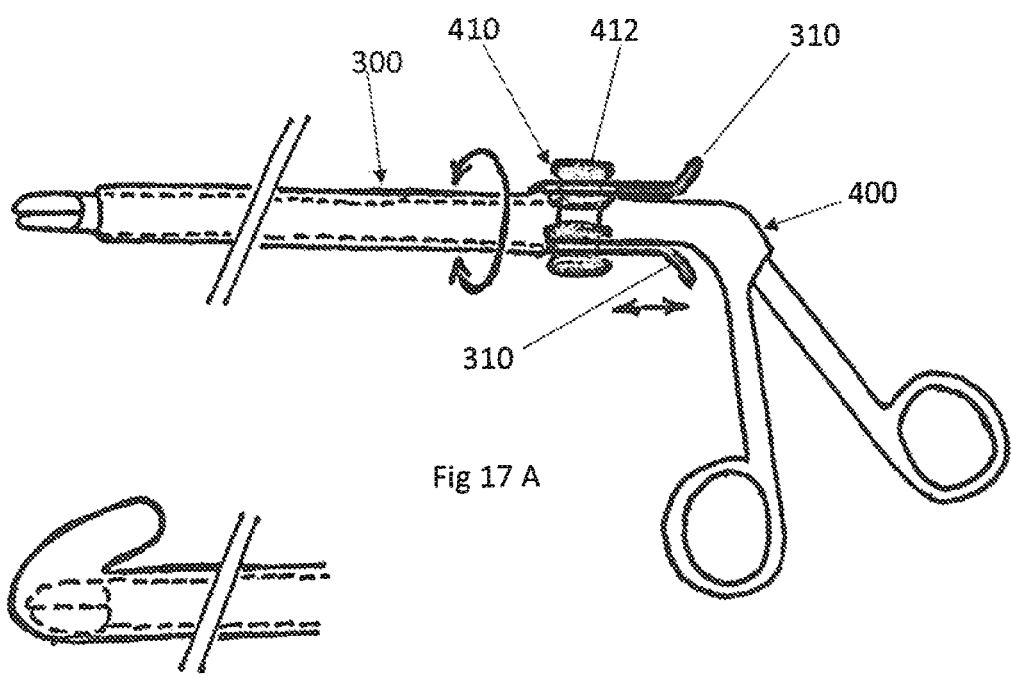
FIGS. 17A and 17B illustrate a knot tying device according to an exemplary embodiment of the present invention disposed on a surgical instrument 400.
Figure 17:
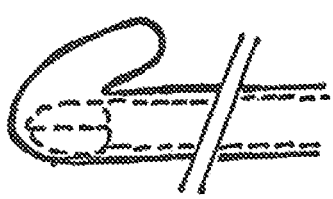

FIGS. 17A and 17B illustrates a knot tying device, generally designated by reference number 300, according to an exemplary embodiment of the present invention disposed on a surgical instrument 400. The surgical instrument 400 includes a rotating mechanism 410 having grip elements 412, such as, for example, ridges or protrusions that allow the clinician to actuate one or more rotating parts of the surgical instrument 400. The knot tying device 300 is structured similar to the previously-described embodiments, but in this case may include one or more arms 310 at the proximal end portion of the knot tying device 300. Each arm 310 may extend between or otherwise engage with the grip elements 412 of the rotating mechanism 410 of the surgical instrument 400. As shown in FIG. 17A, when retracted, the knot tying device 300 rotates together with the surgical instrument 400. This does not cause any interference with the operation of the surgical instrument 400 since the knot tying device 300 is pulled back from the distal tip portion of the surgical instrument 400 and therefore allows for the free use of the acting tip. As shown in FIG. 17B, when the knot tying device 300 is deployed, the rotating mechanism 410 (in contact with the one or more arms 310 of the knot tying device 300) can be used to rotate the knot tying device 300 to manipulate the suture ends and construct knots. In this configuration, the acting tip of the surgical instrument 400 does not interfere with operation of the knot tying device 300 since the distal end portion of the knot tying device 300 covers the acting tip. The one or more arms 310 might also allow for the deployment and retraction of the knot tying device 300. It should be appreciated that the knot tying device 300 does not need to be used with a surgical instrument having a rotating mechanism, in which case the one or more arms 310 may be used to rotate, deploy and/or retract the knot tying device 300 independently of any associated rotation or movement of the instrument on which it is mounted. Further, the length, width and/or shape of the one or more arms 310 may be varied based on need and the instrument being used.

In various exemplary embodiments, the material used to form the knot tying device is strong enough to avoid bending when tying knots.

In various exemplary embodiments, the material used to form the knot tying device is soft enough so that it will not injure viscera or structures it touches while being used.

In various exemplary embodiments, the distal end portion of the knot tying device may have a slightly smaller diameter than the proximal end portion to facilitate the suture flow once the knot is developed and the device is retracted.

In various exemplary embodiments, the knot tying device may include a handle that allows the clinician to move the sheath longitudinally (and also circularly), and the handle is sufficiently long and positioned sufficiently close to the instrument being used so that it does not interfere with operation of the instrument and the clinician does not need to struggle or push against tissues or trocars when the knot-tying device is extended or retracted while tying the knot.

In various exemplary embodiments, in order to accommodate instruments of various lengths, the knot tying device might have one or more of the following: expandable arms, folding arms, curling arms, telescoping arms, a telescoping shaft, an expandable shaft, an expandable bent/curved site, malleable arms, arms that adjust to the contour of the instrument and combinations thereof. The expandable portion might be, for example, telescoping, accordioned (similar to a drinking straw) and/or coiled.

In various exemplary embodiments, the knot tying device might allow for clockwise and/or counter-clockwise rotation.

In various exemplary embodiments, the knot tying device might have varying degrees of bend/angulation based upon need. The angulation might be pre-determined/fixed or adjustable.

In various exemplary embodiments, the knot-tying device might include a mechanism to prevent the device from moving or becoming loose/dislodged while it is retracted and the surgical instrument on which it is mounted is being used, or while it is deployed and a knot is being tied. The securing/anchoring might be activated/deactivated by a clinician based on ongoing needs and use. Examples of such securing/anchoring mechanisms may include but are not limited to the following types: toothed surfaces, hooks, hook-and-loop fastener (e.g., VELCRO®), securing lock, adhesive surface, ball and socket, click mechanism, peg-in-groove coupling, rail-in-groove, interference fit, ratchet/teeth, magnet, hook, tie, elastic band, screw/twist and combinations thereof.

It should be appreciated that although the knot tying device 1 has a bend/angulation in its resting configuration (prior to being mounted on an instrument), in other exemplary embodiments the knot-tying device is straight in its resting configuration and acquires the bend/angulation only when deployed.

In various exemplary embodiments, the knot tying device might include a coil (or other configuration that could be deployed and would allow an easier construction of a knot) rather than a bend/angulation at its tip. This variation might include a rotational motion to disengage the suture from the coil as the device is retracted and the knot is constructed.

In various exemplary embodiments, the knot-tying device can be used in a number of ways, including, for example:
using in a fixed position by simply deploying it (without rotating it);
using by deploying and rotating it (clockwise and/or counterclockwise);
rotating by rotating the arms/handles of the device, independent of the instrument on which it is mounted;
rotating by keeping the arms/handles of the device close to the rotational mechanism of the instrument, and rotating the mechanism together with the knot-tying device (the active end of the laparoscopic instrument is covered by the knot-tying device, and rotating the instrument and the device together will have no detrimental effect);
rotating by rotating the entire instrument on which it is mounted; and
a combination of the above.

Figure 18:
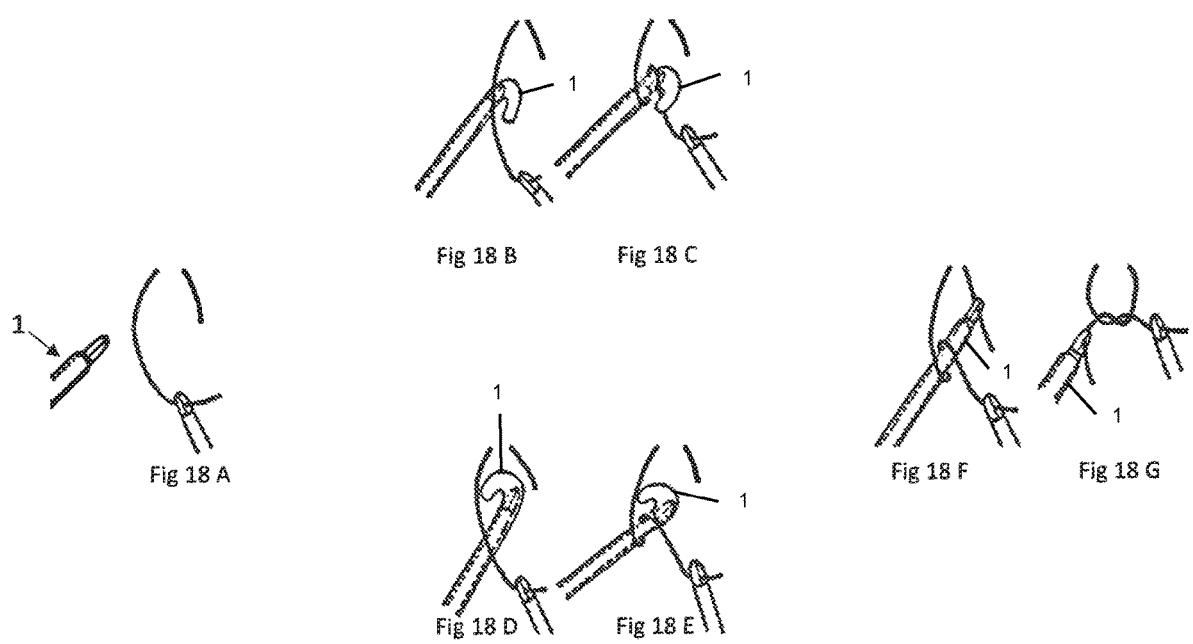
FIGS. 18A-18G show a knot tying procedure using a knot tying device according to an exemplary embodiment of the invention.

FIGS. 18A-18G show a knot tying procedure using the knot tying device 1 (or 300) according to an exemplary embodiment of the invention. As shown in FIG. 18A, the knot tying device 1 disposed on a first surgical instrument is initially in a retracted configuration, while a second surgical instrument is used to grasp a suture end. The knot tying device 1 is then deployed so that the hooked end of the knot tying device 1 extends beyond the distal end of the first surgical instrument. The suture end is then looped around the hook shaped distal end portion of the knot tying device 1 using the second surgical instrument. The hook shaped distal end portion prevents the suture from coming loose. These steps of the procedure may take place with the hook shaped distal end portion of the knot tying device 1 either facing the second surgical instrument (FIGS. 18B and 18C), facing away from the second surgical instrument (FIGS. 18D and 18E) or disposed in any other configuration. As shown in FIGS. 18F and 18G, the first surgical instrument is then advanced (or the knot tying device is retracted), allowing for the tip of the first surgical instrument to grasp the other free suture end. The knot can then be constructed.

FIGS. 19A-19H show variations on the configuration of the proximal end portion of the knot tying device 1 to accommodate surgical instruments with components such as rotational mechanisms or other mechanism that might protrude from the central shaft of the instrument.

In the configuration shown in FIG. 19A, the proximal end portion of the knot tying device 1 is cone-shaped so as to expand around the protruding mechanism of the instrument.

As shown in FIG. 19B, the arms/handles of the device 1 may be malleable so that the clinician might adapt them to the desired contour. This variation has the advantage that the device can be used interchangeably among instruments with different shapes and sizes. This approach would also allow for the coiling of the arms/handles in cases where a shorter length is desired, as well as for the uncoiling when the original length is once again needed. The arms may also have a telescoping mechanism that allows for the expansion or contraction of the arms as needed based on shape of the underlying surgical instrument on which it is mounted.

As shown in FIG. 19C, a portion of the sheath might be expandable so as to adapt to instruments having varying shapes and sizes.

As shown in FIGS. 19D-19E, the proximal end portion of the knot tying device 1 might include one or more perforated lines, and the clinician may separate the sheath along the perforated lines to form the arms/handles. This variation has the advantage that the clinician is able to develop on an individual basis (based on the specific characteristics of the instrument) the desired length and width of the arms/handles.

Figure 19:
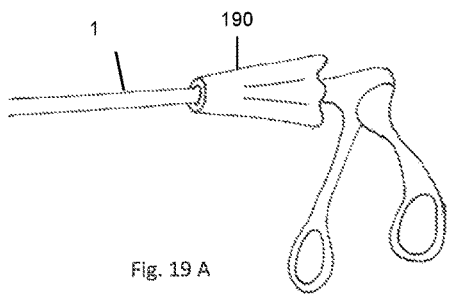
FIGS. 19A-19H show variations on the configuration of the proximal end portion of a knot tying device according to exemplary embodiments of the present invention.
Figure 19:
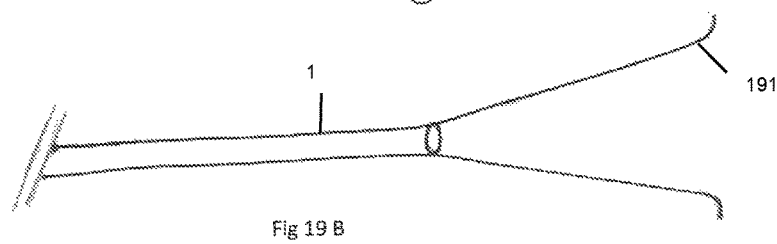
Figure 19:
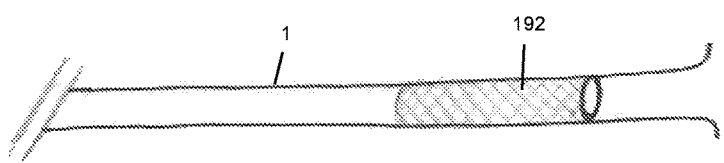
Figure 19:
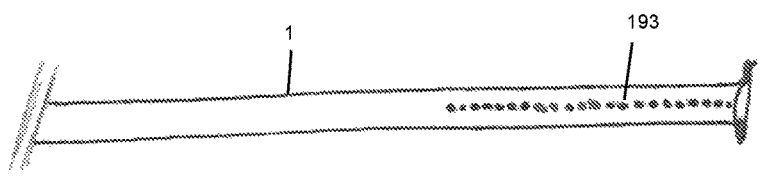
Figure 19:
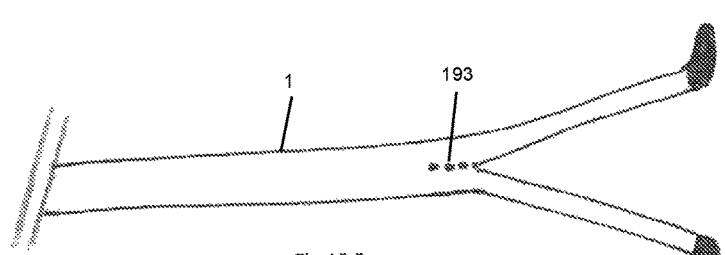
Figure 19:
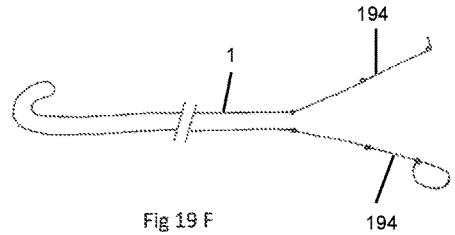
Figure 19:
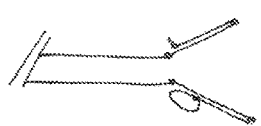
Figure 19:
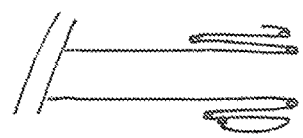

As shown in FIG. 19 F-H, the arms/handles of the device may fold on themselves one or more times. This variation has an advantage that when not in use, the knot-tying device can have minimal to no interference with the instrument.

Figure 20:
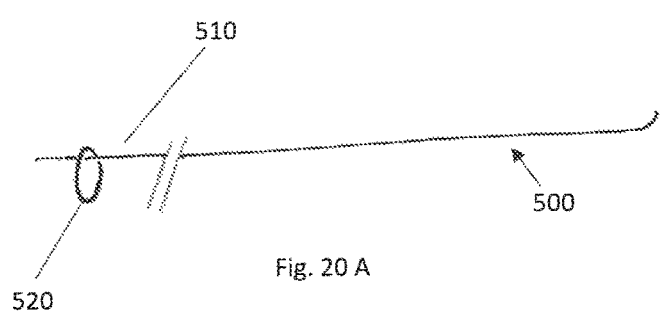
FIGS. 20A-20C shows a knot tying device according to an exemplary embodiment of the present invention.
Figure 20:
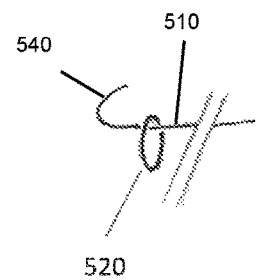
Figure 20:
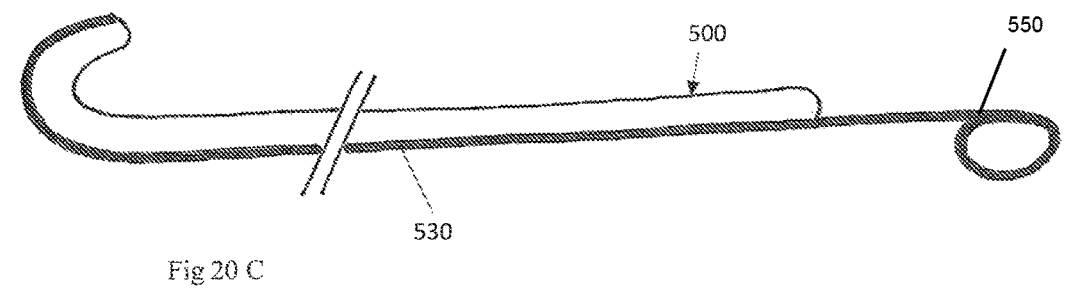

FIGS. 20A-20C shows a knot tying device, generally designated by reference number 500, according to another exemplary embodiment of the present invention. In FIGS. 20A-20B, the knot tying device 500 may have a wire-like main body 510. The main body 510 may be attached with a clip 520 (e.g., a ring or bracket) to a laparoscopic instrument to mount the device 500 on the instrument. As shown in FIG. 20B, when a certain length of the device 500 is deployed, a pre-formed angulation in the device 500 is released. Retracting the device 500 results in the clip 520 once again holding the angulation against the instrument (as shown in FIG. 20A). In FIG. 20C, the knot tying device 500 is constructed with a pre-bent/angled thin rod (530) (or rods) on one side, attached to the sheath. The rod (or rods) may extend along the length of the sheath to form the arm/handle (or arms/handles) of the device. The rod is straightened when in the retracted position, and acquires its baseline bent/angled configuration when deployed. In this regard, the rod may be made of a material that would allow for its straightening and subsequent return to the original bent/angled configuration. The arm/handle may bend, retract, telescope and/or take on one or more other configurations based on preference and/or need of the operator.

Figure 21:
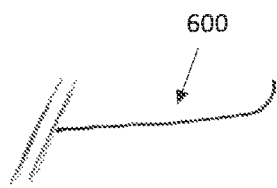
FIGS. 21A-21B shows a knot tying device according to an exemplary embodiment of the present invention.
Figure 21:
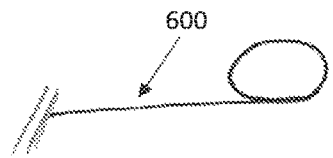

FIGS. 21A-21B shows a knot tying device, generally designated by reference number 600, according to another exemplary embodiment of the present invention. The knot tying device 600 includes an arm/handle in the form of a ring for contact with the clinician's finger.

Figure 22:
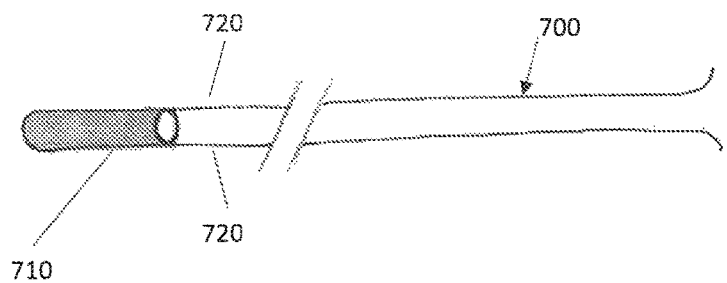
FIGS. 22A-22B shows a knot tying device according to an exemplary embodiment of the present invention.
Figure 22:
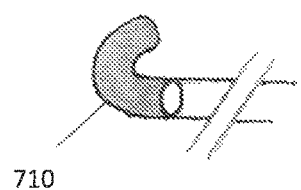

FIGS. 22A-22B shows a knot tying device, generally designated by reference number 700, according to another exemplary embodiment of the present invention. The knot tying device 700 includes a distal end portion in the form of a sheath 710 and a proximal end portion made up of one or more wire-like elements 720 that may be used to actuate the device 700. Deploying the device 700 causes the sheath 710 to acquire its bent/angled shape as it protrudes beyond the tip of the instrument on which it is mounted.

Figure 23A:
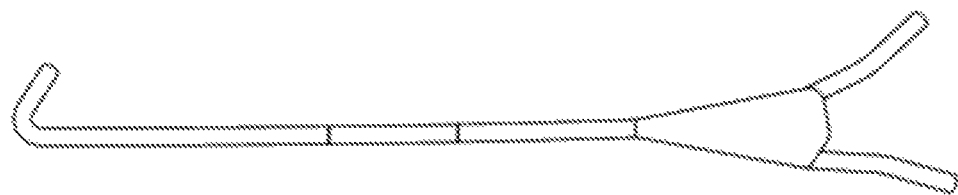
FIGS. 23A-23O are photographs of a prototype of a knot tying device according to an exemplary embodiment of the present invention.
Figure 23B:
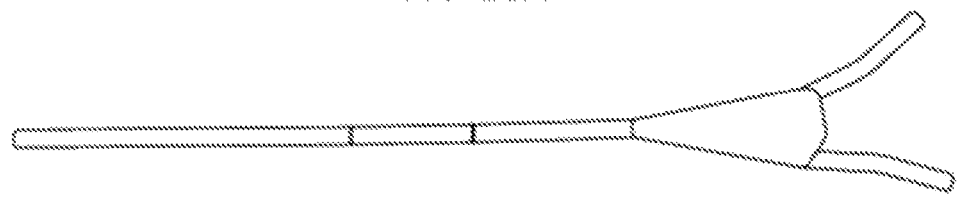
Figure 23C:
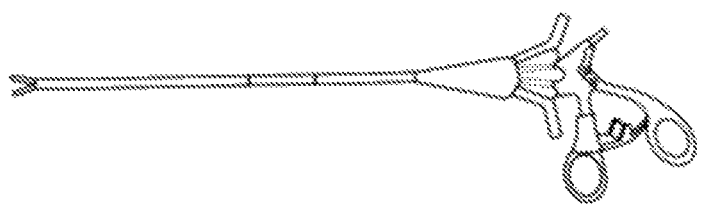
Figure 23D:
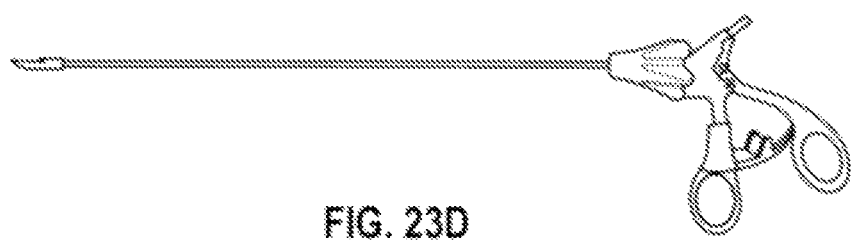
Figure 23E:
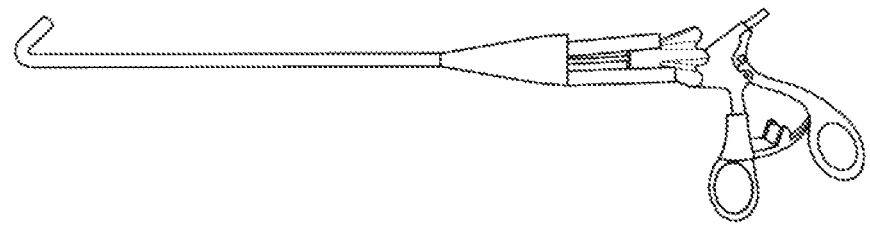
Figure 23F:
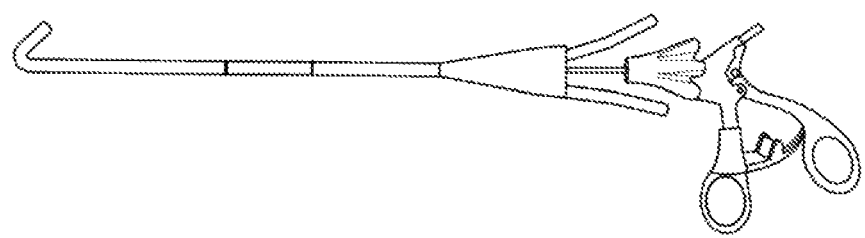
Figure 23G:
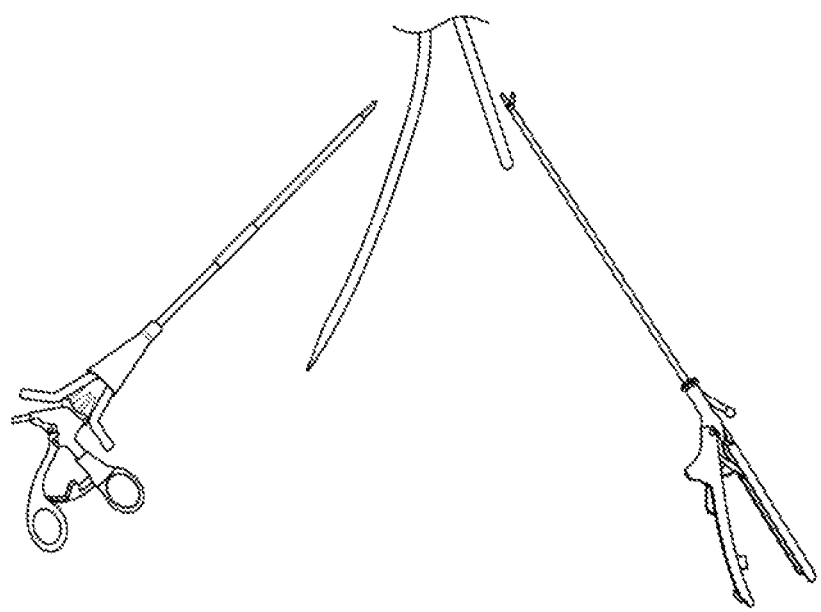
Figure 23H:
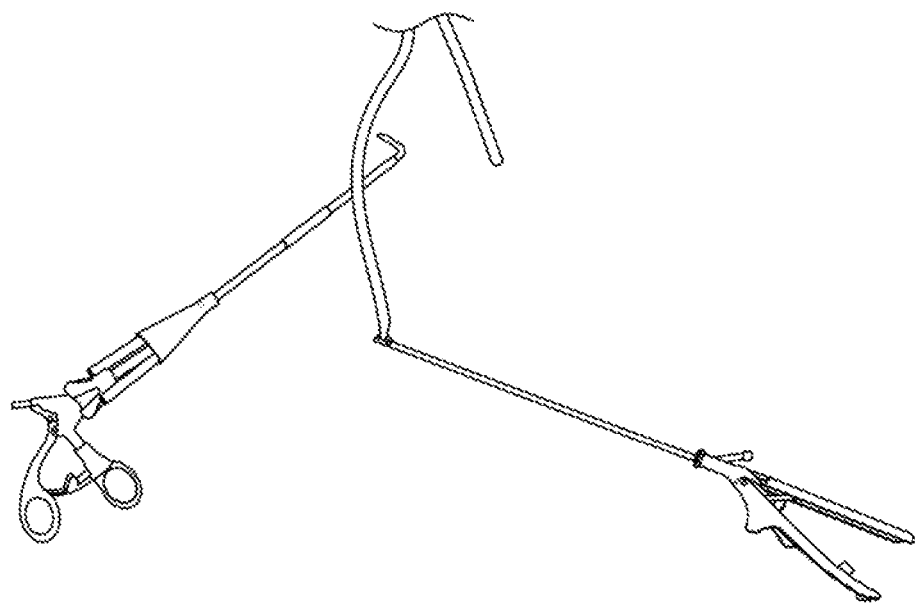
Figure 23I:
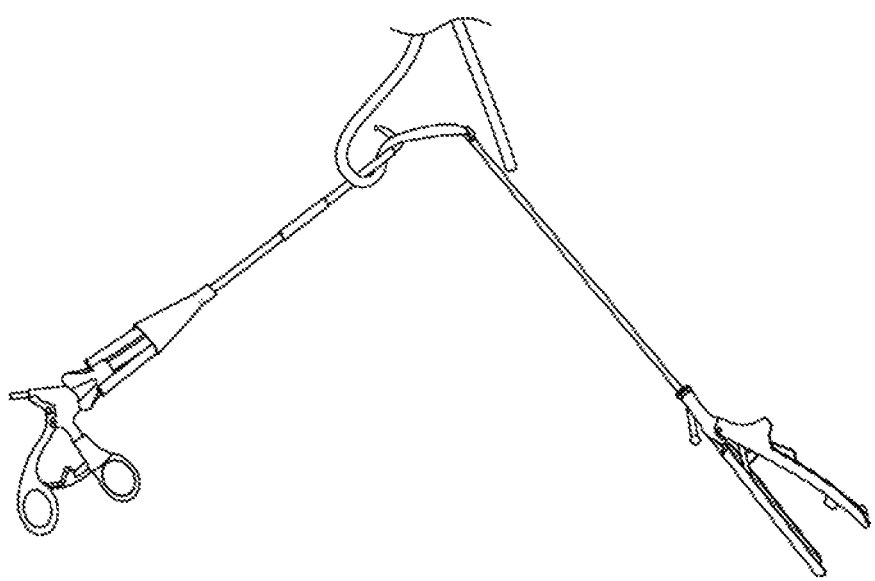
Figure 23J:
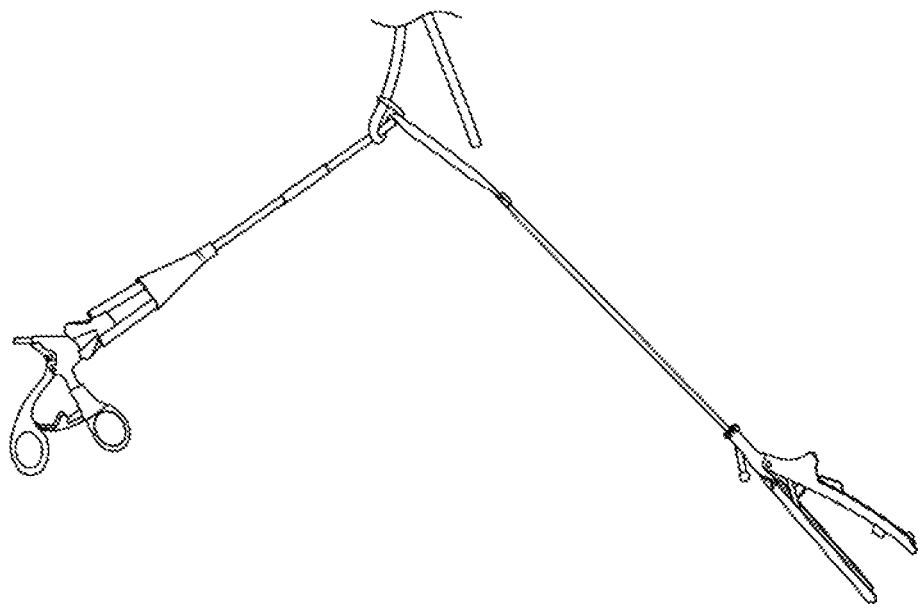
Figure 23K:
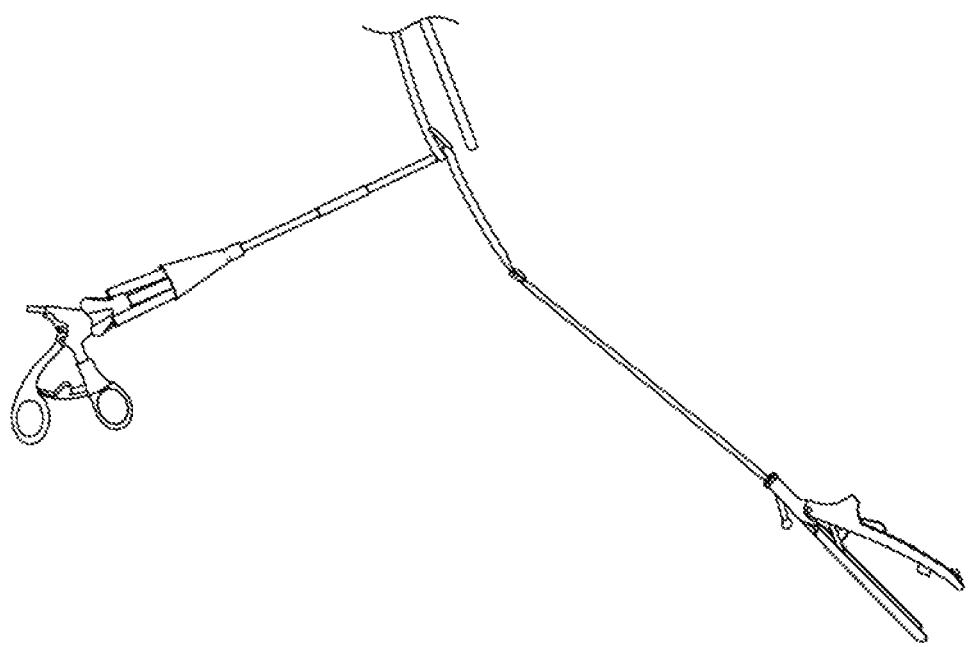
Figure 23L:
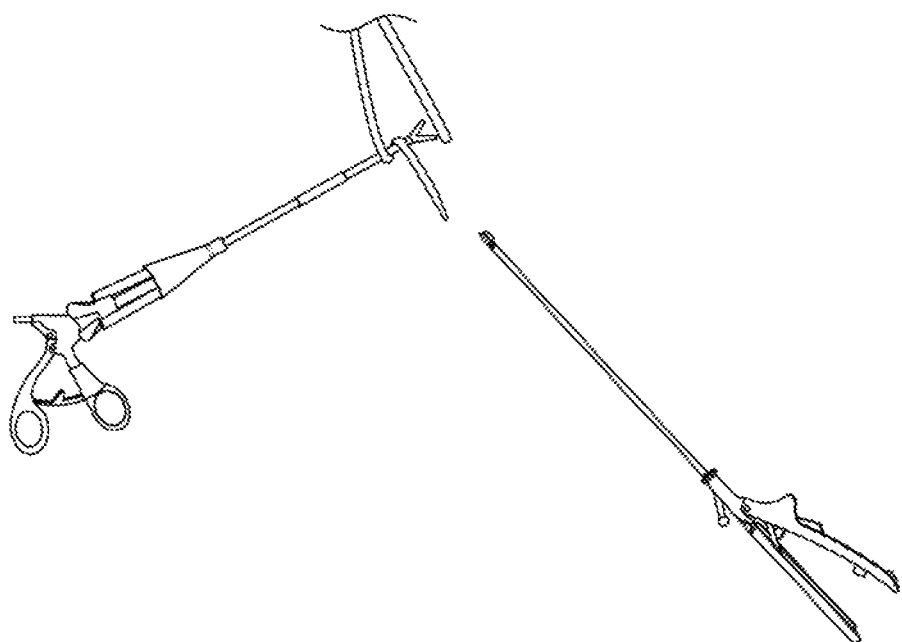
Figure 23M:
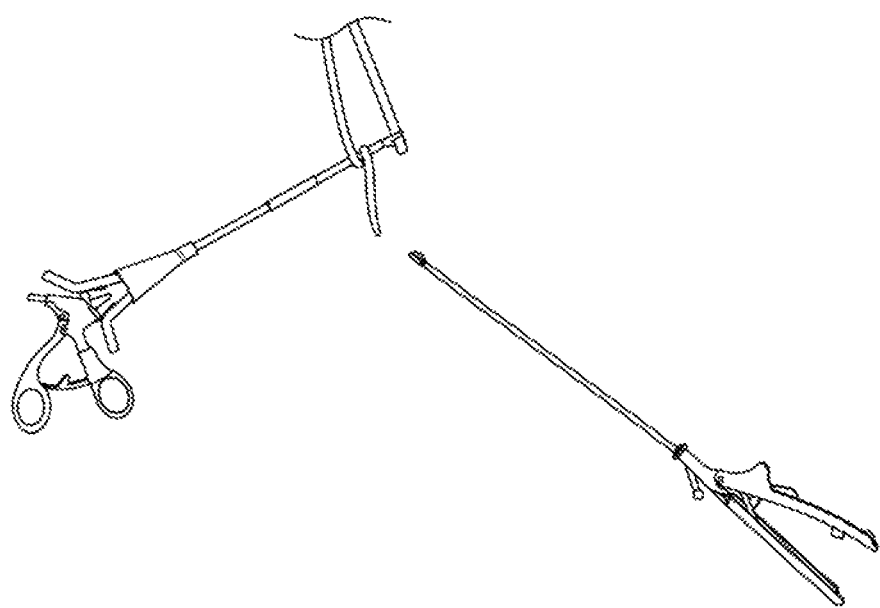
Figure 23N:
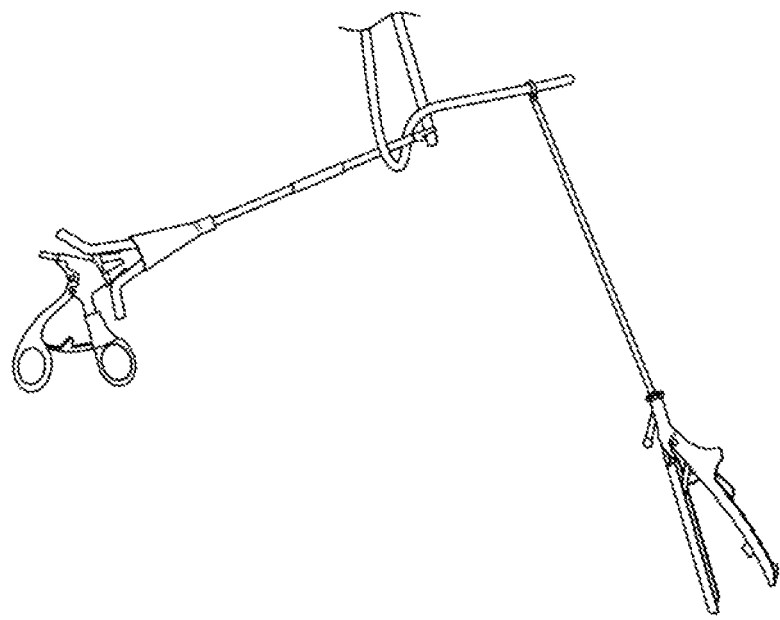
Figure 23O:
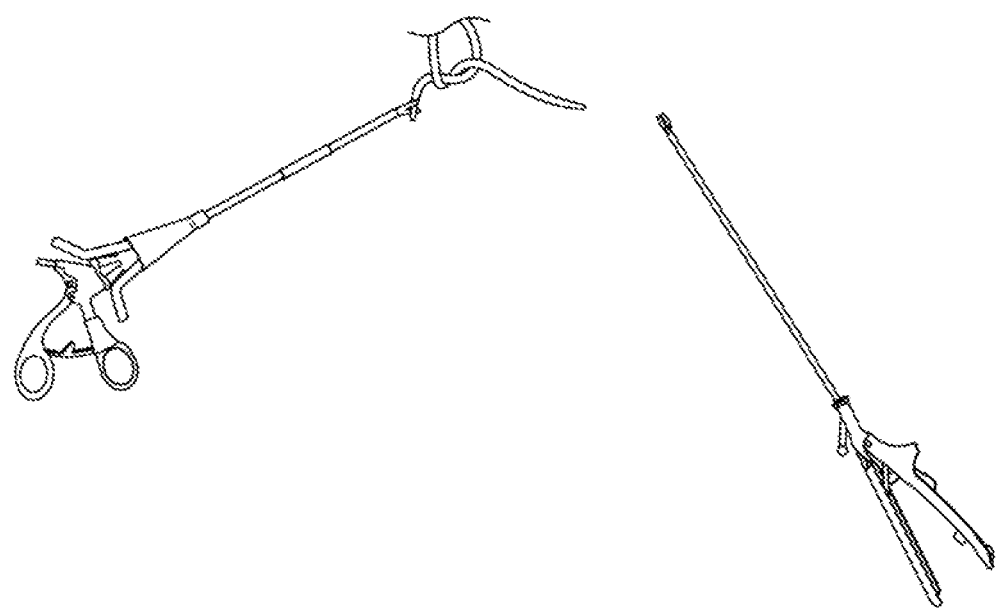
Figure 25:
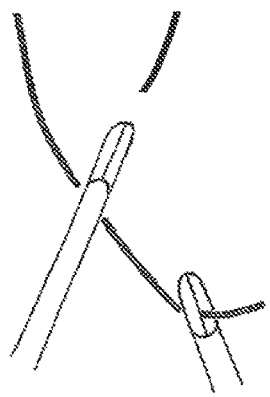
FIGS. 25A-25I illustrate a knot tying device that does not incorporate the use of a sheath but rather includes a hook shaped distal end portion that may be manipulated while tying a knot and subsequently straightened again as the knot is completed.
Figure 25:
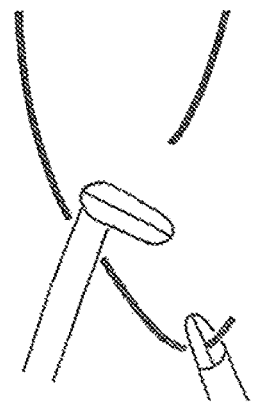
Figure 25:
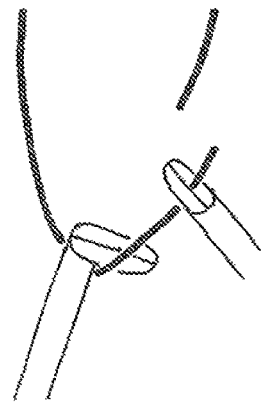
Figure 25:
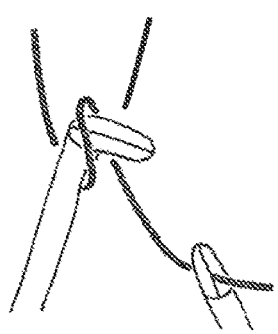
Figure 25:
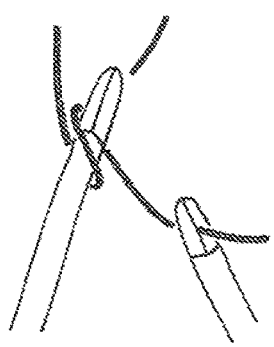
Figure 25:
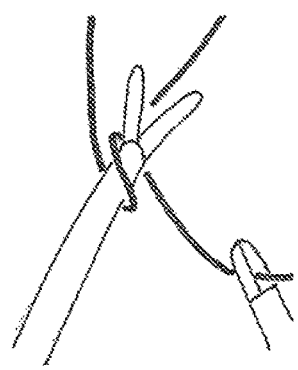
Figure 25:
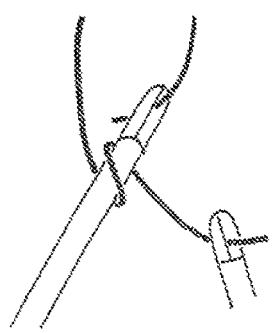
Figure 25:
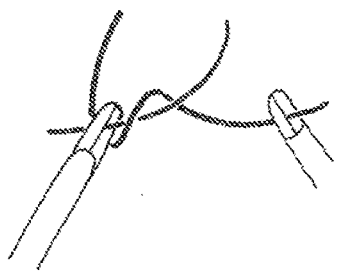
Figure 25:
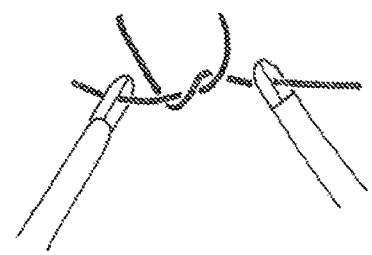

FIGS. 23A-23O are photographs of a prototype of a knot tying device according to an exemplary embodiment of the present invention. FIG. 23A shows the device with the bend/curvature as its baseline configuration. FIG. 23B shows a variation with no bend/curvature at baseline. FIG. 23C shows the device in its retracted configuration side by side with a laparoscopic instrument. Note that the malleable arms/handles of the device shown in this example allow the operator to mold and adapt them to each individual instrument. FIG. 23D shows the device in its deployed configuration side by side with a laparoscopic instrument. Note the corresponding lengths of device and instrument.

As shown in FIGS. 23E and 23F, the knot-tying device has been mounted on the instrument and is shown in the deployed position. Note that the arms/handles of the device can be close to (FIG. 23E) or distant from (FIG. 23F) the rotational site of the laparoscopic instrument based on the preference of the clinician. The presence of the device does not affect the rotation of the instrument since both (knot tying device and shaft of the instrument) can rotate together. Alternatively, the knot tying device and instrument may rotate individually independent of one another.

The knot-tying device could be (based on the preference of the operator): used in a fixed position by simply deploying it (without rotating it); used by deploying and rotating it (clockwise and/or counterclockwise as shown in the images); rotated by rotating the arms/handles of the device, independent of the instrument on which it is mounted; rotated by keeping the arms/handles of the device close to the rotational mechanism of the instrument, and rotating the mechanism together with the knot-tying device (the active end of the laparoscopic instrument is covered by the knot-tying device, and rotating the instrument and the device together will have no detrimental effect); rotated by rotating the entire instrument on which it is mounted; a combination of the above.

FIG. 23G shows the knot-tying device (mounted on the instrument on the left side of the image) in the retracted position. Note that in this specific example, the arms/handles of the knot tying device have been partially flexed to avoid any interference with the operation of the handles of the laparoscopic instrument. Alternatively, the arms/handles could be partially or fully folded on themselves, or otherwise modified as previously described.

FIG. 23H shows the knot-tying device deployed using the arms/handles, that now are extended. Note the bend/angulation at the distal end of the deployed knot-tying device. The tip of the laparoscopic instrument is now completely covered by the knot-tying device. The instrument on the right side of the image has grasped one end of the suture to be tied and placed it anterior to the device.

As shown in FIGS. 23I-23K, the instrument on the right side of the image loops one limb of the suture to be tied around the distal end of the deployed knot-tying device (arrows). Note that the curve/angulation of the knot-tying device prevents the suture from becoming loose and slipping out of position, ensuring a quick and accurate knot formation.

As shown in FIGS. 23L-23M, as the knot-tying device is retracted (note the arms/handles back on their original position), the instrument onto which it is mounted is advanced toward the other (free) limb (end) of the suture to be tied. The tip of the instrument is again exposed, and grabs the other (free) end of the suture. Note that this process has been accomplished without disturbing the end of the suture looped around the knot-tying device. As shown in FIGS. 23N-23O, the knot is then tightened and finalized.

In other exemplary embodiments of the present invention, the knot tying device might be built into a laparoscopic surgical instrument (such as, for example, a needle driver, dissector, etc.) so that the knot tying device and the surgical instrument form a unitary structure (see FIGS. 24A-24B). In this specific example the knot tying device component 800 of the instrument 810 is deployed (FIG. 24B) and subsequently retracted (FIG. 24A) by moving an actuating mechanism, such as arm/handle/button 820, back and forth. When the knot tying component is retracted, the jaws 830 of the instrument depicted in this example can be opened freely. Other types of instruments may also have a knot tying device built into them, and the knot tying device may include actuating mechanisms different from the one shown in this specific example. The knot tying device in these embodiments may not incorporate the use of sheath, but may include one or more of the concepts previously described, including a hook shaped distal end portion that may be manipulated by a user while tying a knot and subsequently straightened again as the knot is completed (see FIGS. 25A-25I). An instrument incorporating a knot tying device may be disposable or reusable.

A knot tying device according to another exemplary embodiment of the present invention is made up of a magnetic/electromagnetic component that can be an instrument by itself, part of an instrument, or placed over any laparoscopic/robotic instruments (such as a sheath placed over graspers, needle drivers, dissectors, etc.). Although the description herein is provided in the context of laparoscopic/robotic procedures, it should be appreciated that the inventive knot tying device may be suitable for use with other types of procedures, such as, for example, telesurgery, battlefield procedures, interventional radiology, open procedures, non-medical procedures, and veterinary medicine.

FIGS. 26A-26C are perspective views of a knot tying device, generally designated by reference number 1000, according to an exemplary embodiment of the present invention. The knot tying device 1000 includes one or more magnetic elements 1010. The one or more magnetic elements 1010 may include any type of magnet, such as, for example, permanent magnets and electromagnets. The magnetic elements 1010 can be single or multiple, of various shapes and sizes, located on various locations on the body of the instrument 1100, circumferential or non-circumferential, incorporated as part of the instrument 1100 or removable or as part of a sheath disposed on the instrument 1100.

FIGS. 27A and 27B are perspective views of a knot tying device according to an exemplary embodiment of the present invention disposed on a surgical instrument 1100. In this instance the magnetic element 1010 is cylindrical and removable from the instrument 1100. The magnetic element 1010 can be slid along the body of the instrument 1100 based on the needs of the operator. The magnetic element 1010 may have an elastic and/or adhesive part 1200 of variable size and shape that allows for the magnetic element 1010 to adjust to various instruments and to remain in a set position. Alternatively, the magnetic element 1010 may be moved along and/or around the instrument 1100 as needed by the operator.

FIGS. 28A and 28B show a knot tying device, generally designated by reference number 2000, according to another exemplary embodiment of the present invention. The knot tying device 2000 may include a main body 2301 that includes a magnetic element. The main body 2301 may be cylindrical or of other shapes and may be connected to an arm 2300. The arm 2300 may be a wire-like (or other shape) projection that extends from one side of the main body 2301. The device 2301 if cylindrical in shape can be placed directly on a surgical instrument (FIG. 3A). Otherwise, the device 2301 may be held in place by the arm 2300 as well as by a clip 2320 (e.g., a ring or bracket) to a laparoscopic/robotic instrument. The arm 2300 may allow the operator to move the device along the length of the instrument. The arm 2300 may bend, retract, telescope and/or take on one or more other configurations based on preference and/or need of the operator.

FIGS. 29A-29J show a knot tying device according to an exemplary embodiment of the present invention made up of a sheath 3000 that can be placed over any laparoscopic/robotic instrument 1100 (such as graspers, needle drivers, dissectors, etc.). A magnetic element 3010 can be located at various sites along the sheath 3000. The magnetic element 3010 can be single or multiple, cylindrical or of various other shapes.

The distal end of the sheath 3000 may have a bend (FIGS. 29A-29G) whose curvature can be overcome by sliding the instrument that is being placed within it (similar to a drinking straw being straightened).

In an exemplary embodiment, the magnetic element 3010 is attached to the sheath 3000 which may be made using a molding process, resulting in the distal end portion 3420 of the sheath 3000 taking on a hook or bent shape. Due to the flexible nature of the material, the sheath 3000 is able to elastically deform. For example, as shown in FIGS. 29D and 29F, the knot tying device may be flexed over a surgical instrument 1100 so that the surgical instrument 1100 is essentially sheathed with the hook shaped distal end portion 3420 extending beyond the distal end portion of the surgical instrument 1100. As shown in FIGS. 29C, 29E, and 29G, the sheath 3000 may be pulled back in the proximal direction over the surgical instrument 1100 so that the tool end of the surgical instrument 1100 is exposed for use. In this configuration, the distal end portion 3420 of the knot tying device is elastically deformed into a straightened shape. Alternatively, the sheath may have a fixed straight configuration (FIGS. 29H-29J).

In exemplary embodiments, the knot tying device, that could include potentially a sheath 3000 and/or arm 2300 (as previously described), may be activated to have linear motion to allow for back and forth motion on the surgical instrument, and/or rotational motion to allow for the device or a sheath or arm/handle associated with the device to rotate in a clockwise and/or counter-clockwise motion to create a knot. The linear and rotational motions may be independent of and/or dependent on one another.

Alternatively, the knot tying device, that could include potentially a sheath 3000 and/or arm 2300 (as previously described), may be activated to have only a linear motion relative to the instrument, and the rotation of the bend may be achieved by rotating the entire instrument.

Alternatively, the knot tying device, that could include potentially a sheath 3000 and/or arm 2300 (as previously described), may be activated to have only a circular motion relative to the instrument, and the linear motion may be achieved by moving the entire instrument in an antegrade or retrograde fashion.

Alternatively, the instrument and/or sheath may have no motion at all and remain static.

In exemplary embodiments, the knot tying device and (if present) associated components such as sheaths or arms may be deployed/activated manually and/or through the use of mechanical, hydraulic, pneumatic, sonic, ultrasonic or electronic components, or combinations thereof. It should be appreciated that the deployment/activation mechanism is not limited to the types listed herein.

FIGS. 30A-30H show a knot tying procedure using the knot tying device 1000 according to an exemplary embodiment of the invention. In FIG. 30A, after the suture is placed, the ends to be tied are addressed. At this point, the magnetic element 1010 of the knot tying device is in proximity to the needle 6000 associated with one end of the suture. After the needle adheres magnetically to the device, the device rotates (either clockwise of counter-clockwise) as it moves (deploys) proximally, bringing the needle together with it (FIGS. 30B and 30C). The instrument then grabs the other (free) end of the suture (FIGS. 30D and 30E). Another instrument grabs the needle and pulls it away from the magnetic element 1010 of the knot tying device (FIGS. 30F and 30G). The knot is then completed (FIG. 30H). The device may subsequently rotate and retract back to its original position.

The knot tying device is rotated (clockwise in this example) and turned circumferentially, thereby creating at least one loop in the end of the suture. Alternatively, the suture can be looped one or more times.

FIGS. 31A and 31B illustrate a knot tying device 4000 according to an exemplary embodiment of the present invention disposed on a surgical instrument 7000. The surgical instrument 7000 includes a rotating mechanism 7710 having grip elements 7712, such as, for example, ridges or protrusions that allow the clinician to actuate one or more rotating parts of the surgical instrument 7000. The knot tying device 4000 is structured similar to the previously-described embodiments, but in this case may include one or more arms (or activating buttons) 4810 at the proximal end portion of the knot tying device 4000. Each arm/button 4810 may extend between or otherwise engage with the grip elements 7712 of the rotating mechanism 7710 of the surgical instrument 7000. As shown in FIG. 31A, when retracted, the knot tying device 4000 rotates together with the surgical instrument 7000. This does not cause any interference with the operation of the surgical instrument 7000 since the knot tying device 4000 is pulled back from the distal tip portion of the surgical instrument 7000 and therefore allows for the free use of the acting tip. As shown in FIG. 31B, when the knot tying device 4000 is deployed, the rotating mechanism 7710 (in contact with the one or more arms/buttons 4810 of the knot tying device 4000) can potentially be used to rotate the knot tying device 4000 to manipulate the suture ends and construct knots. In this configuration, the acting tip of the surgical instrument 7000 does not interfere with operation of the knot tying device 4000. The one or more arms/buttons 4810 might also allow for the deployment and retraction of the knot tying device 4000. It should be appreciated that the knot tying device 4000 does not need to be used with a surgical instrument having a rotating mechanism, in which case the one or more arms/buttons 4810 may be used to rotate, deploy and/or retract the knot tying device 4000 independently of any associated rotation or movement of the instrument on which it is mounted. Further, the length, size, width and/or shape of the one or more arms/buttons 4810 may be varied based on need and the type of instrument being used.

Alternatively, the knot tying device may be activated by a mechanical (or other) mechanism.

Figure 32D:
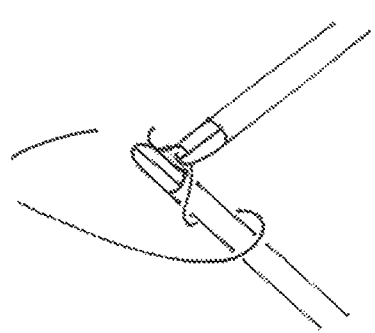
FIGS. 32A-32G show possible variations in the configuration of the proximal portion of the knot tying device according to an exemplary embodiment of the present invention.
Figure 32C:
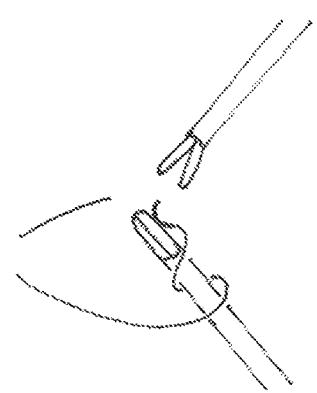
Figure 32B:
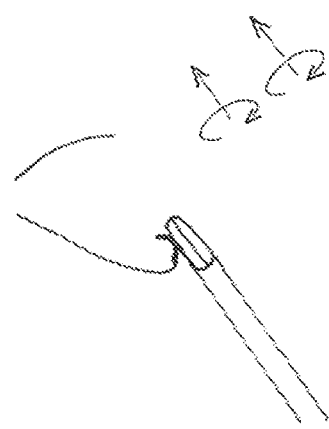
Figure 32A:
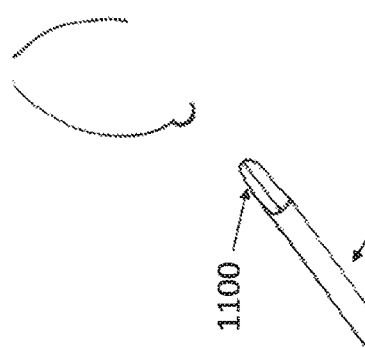
Figure 32G:
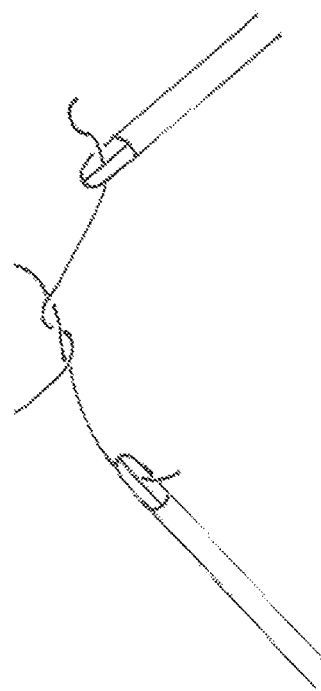
Figure 32F:
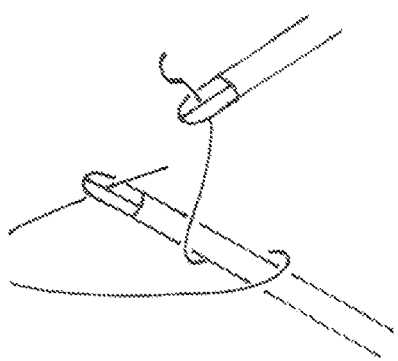
Figure 32E:
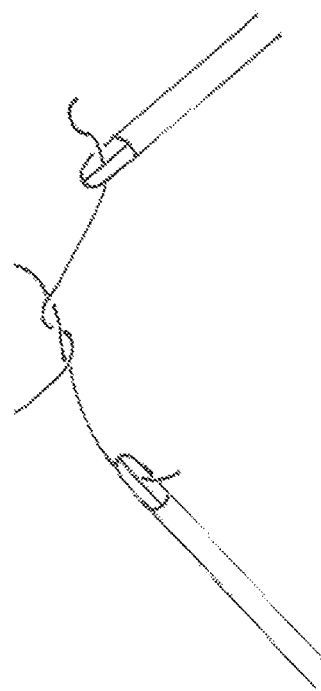

FIGS. 32A-32G show a knot tying procedure using the knot tying device 5000 according to an exemplary embodiment of the invention. As shown in FIG. 32A, after the suture is placed, the ends to be tied are addressed. In this embodiment, the entirety of the knot tying device 5000 may be magnetic, or both jaws of the instrument 1100, or only one of the jaws may be magnetic. After the needle adheres magnetically to the device, the device rotates (either clockwise of counter-clockwise) as it moves (deploys) proximally, bringing the needle together with it (FIGS. 32B and 32C). Another instrument grabs the needle and pulls it away from the magnetic/electromagnetic component of the knot tying device (FIG. 32D). The instrument 1100 with the knot tying device then grabs the other (free) end of the suture (FIGS. 32E and 32F). The knot is then completed (FIG. 32G).

The knot tying device 5000 is rotated (clockwise in this example) and turned circumferentially, thereby creating at least one loop in the end of the suture. Alternatively, the suture can be looped one or more times.

This embodiment would also be especially useful in robotic procedures, where one or both arms of the jaw of the robotic instrument could be magnetized (partially or permanently) in order to create the knot.

Figure 33B:
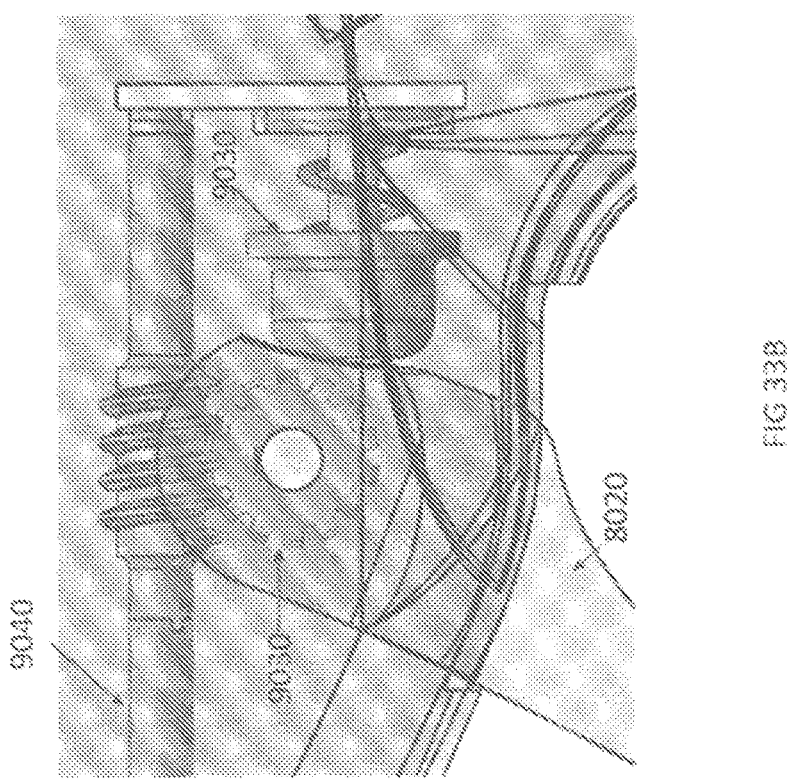
FIGS. 33A-33B are perspective views of a knot tying device according to an exemplary embodiment of the present invention.
Figure 33A:
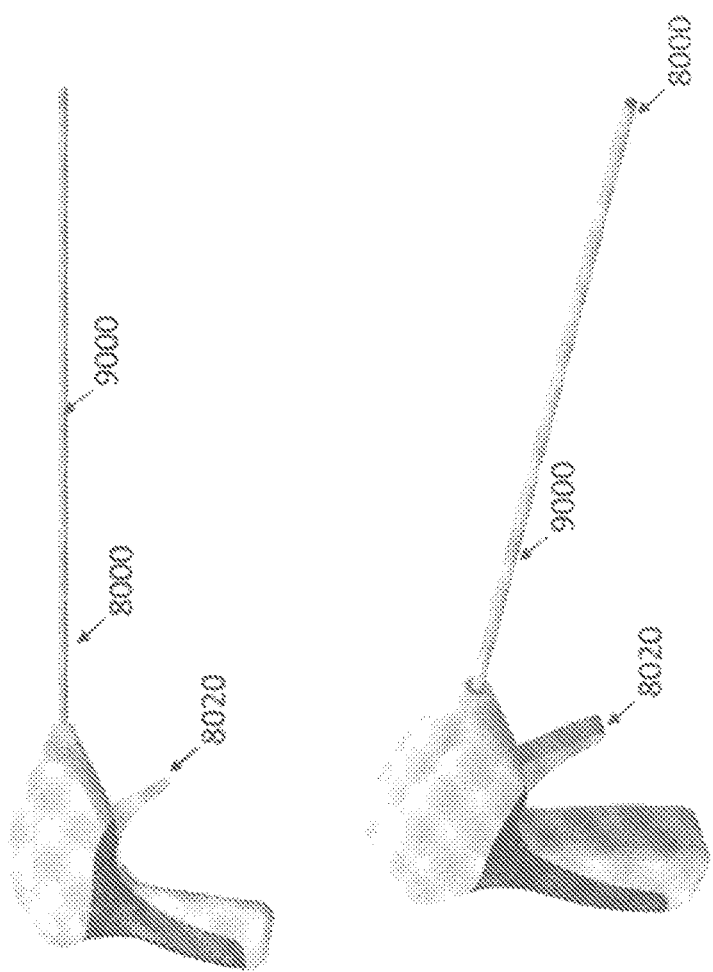
Figure 34:
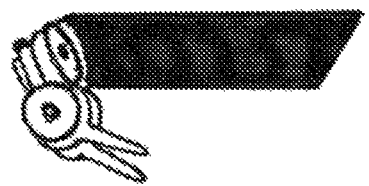
FIGS. 34A-34F show various surgical instruments as implemented in accordance with exemplary embodiments of the present invention.
Figure 34:
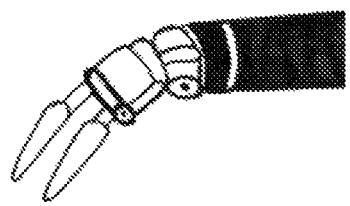
Figure 34:
Figure 34:
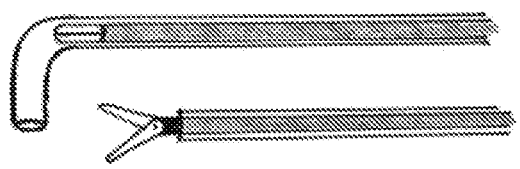
Figure 34:
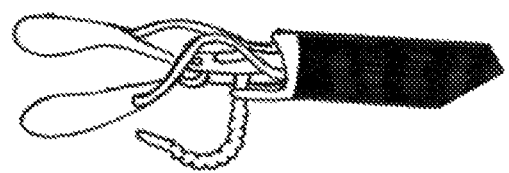

FIGS. 33A-33B illustrate a knot tying device, generally designated by reference number 8000, according to an exemplary embodiment of the present invention disposed on a surgical instrument 9000. Alternatively, the knot tying device may be an instrument by itself. The surgical instrument 9000 includes a rotating mechanism 9040 that allows the clinician to actuate one or more rotating parts of the surgical instrument 9000. The knot tying device 8000 is structured similar to the previously-described embodiments, but in this case may include one or more triggers (or activating buttons) 8020 at the proximal end portion of the knot tying device 8000. Each trigger/button 8020 may extend between or otherwise engage with components 9030 of the rotating mechanism 9040 of the surgical instrument 9000. The rotating mechanism 9040 can potentially be used to rotate the knot tying device 8000 to manipulate the suture ends and construct knots. The one or more trigger/buttons 8020 might also allow for the deployment and retraction of the knot tying device 8000. It should be appreciated that the knot tying device 8000 does not need to be used with a surgical instrument having a rotating mechanism, in which case the one or more trigger/buttons 8020 may be used to rotate, deploy and/or retract the knot tying device 8000 independently of any associated rotation or movement of the instrument on which it is mounted. Further, the length, size, width and/or shape of the one or more trigger/buttons 8020 may be varied based on need and the type of instrument being used.

Alternatively, the knot tying device may be activated not only by mechanical mechanisms but also by other types of mechanisms (e.g., hydraulic, pneumatic, electric, other).

In exemplary embodiments, one or more magnets are incorporated into any regular/routine instrument being used on a daily basis or into the knot tying device. The magnets may be activated as needed or permanently in a magnetized state.

In exemplary embodiments, at least some of the magnets may be built into one, both, or more (if present) of the jaws (limbs) of the instruments being used.

In exemplary embodiments, at least some of the magnets may be built into the body, part of the body, or the entirety of the instrument.

In exemplary embodiments, at least some of the magnets may be a steady state feature, or may be activated at will (such as by pressing a button or other actuator).

In exemplary embodiments, the power for the magnet may be derived from a battery or from an electrical cable.

As explained previously, in exemplary embodiments, the knot tying device may involve magnetizing/electromagnetizing an entire laparoscopic/robotic instrument itself or otherwise a part or parts of the laparoscopic/robotic instrument while performing the tying of the knot, and removing the magnetization/electromagnetization once the maneuver is accomplished.

In exemplary embodiments, the electromagnetization may be an integral and constant part of the instrument.

In exemplary embodiments, the knot tying device may be single-use (disposable) or reusable. In exemplary embodiments in which the knot tying device is made up of more than one component, each component may be interchangeable with a corresponding component on another knot tying device or may be intended for only a particular knot tying device (such as a specific size or type of knot tying device).

In exemplary embodiments, the knot tying device may be moved manually and/or actuated in a variety of ways, using one or more of the following types of mechanisms:

Hydraulic/pneumatic (compressed fluid/gas)
   a. Hand pump
   b. Foot pump
   c. Electric pump
      i. Battery-operated
      ii. Plug in (e.g., line voltage, transformer, etc.)\
   d. Mechanical kinetic/potential energy pump
Cog wheel mechanism (e.g., hand-drill with two cog-wheels and a rotating arm)
Rack and pinion
Torque
Spiral/ratchet screwdriver mechanism
Click pen mechanism
Zipper
Electric
   a. Battery-operated
   b. Plug in (e.g., line voltage, transformer, etc.)
Elastic band—kinetic/potential energy
Coil—kinetic/potential energy, finger activated
Motor/engine
   a. Individual
   b. Interchangeable
   c. Re-usable
      i. Individual
      ii. Interchangeable
Ball point pen/click pen mechanism
Ultrasonic/sonic
Automated drive
Magnetic/electromagnetic
Trigger mechanism In exemplary embodiments, the knot tying device and/or any of its components may include safety measures such as, for example, pressure sensors, alert mechanisms, and/or automatic shut-off upon reaching one or more predetermined limit/s.

In exemplary embodiments, movement may be restricted to advance a specific distance (e.g., 1 cm, 2 cm, 5 cm) and to rotate a specific number of degrees (e.g., 45°, 90°, 180°, etc.) based on need. The parameters may be pre-set/fixed in advance or adjustable at will by the clinician (e.g., pre-set ratchet mechanism, pre-set scale, adjusting button/dial, etc.), either in advance or as needed during the procedure (based on tissues being sutured, type of suture being used, ability of the operator, and other factors).

In exemplary embodiments, the electrical power used to activate movement could also be used to simultaneously (or non-simultaneously) activate the magnet/electromagnet or other components.

In exemplary embodiments, the knot tying device may be made available as part of a kit. For example, the kit may contain one or more knot tying devices having a common size and type or varying sizes and types. The kit may contain additional elements, such as, for example, other types of surgical instruments and an instruction manual. In exemplary embodiments, the knot tying device may be single-use/disposable, while in other embodiments the knot tying device may be reusable. For example, the knot tying device may be sterilized after each use, using any of a variety of sterilization techniques, including, for example, steam under pressure (autoclaving), gamma radiation, dry heat or heat/chemical vapor. Components of the knot-tying device (such as the power supply, electric cables, foot pedal, console, motor, etc.) may also be single use or reusable, and for individual use or interchangeable.

The knot tying device, that could include potentially a sheath 3000 and/or wire-like arm/handle 2300, is preferably a unitary structure and may be made of elastic or non-elastic polymeric or other material, such as, for example, metal, polyethylene, silicone rubber, natural rubber, PVC, polyurethane, polypropylene, polyester, polyether ether ketone, polyphenylsulfone, nylon, and polytetrafluoroethylene (e.g., Teflon). The material is preferably strong and durable enough to withstand the rigors of laparoscopic procedures while maintaining its general shape profile, flexible/rigid enough to perform effectively during use, and delicate enough to avoid injury to surrounding structures it may come in contact with during use. Portions of the sheath 3000 and/or wire-like arm/handle 2300 may be made of different materials to provide variations in properties along the length of the device, for example, variations in flexibility along the length of the device. In this regard, various portions of the device/sheath/arm/handle for example may not need to be as flexible/rigid as other portions of the device.

In exemplary embodiments, in addition to linear and rotational motion, the knot tying device, that could include potentially a sheath 3000 and/or wire-like arm/handle 2300, could also develop various degrees of angulation, telescoping, coiling, flexibility, bending, and/or stiffness based on the specific requirements. Such angulation, telescoping, coiling, flexibility, bending, stiffness, and other properties could occur within the same instrument (and/or sheath/arm), or there could be various instruments (and/or sheaths/arms) with such variations.

The sheath/arm (when present) could be lubricated or otherwise designed to prevent it from sliding. The knot tying device, that could include potentially a sheath 3000 and/or wire-like arm/handle 2300, may be expandable, telescoping, retractable, and/or have an articulation within it. This would allow for it to be adaptable to instruments of various lengths, be adaptable to articulating instrument, and to have telescoping and/or accordion type of systems to allow for expansion, retraction, articulation.

In various exemplary embodiments, the magnet/electromagnet used to form the knot tying device will have various strengths, that may be fixed or variable and be pre-set or regulated to be strong enough to hold various needles.

In various exemplary embodiments, the material used to form the knot tying device is strong enough to avoid unwanted bending or breaking when being used.

In various exemplary embodiments, the material used to form the knot tying device is soft enough so that it will not injure viscera or structures it touches while being used.

In various exemplary embodiments, the distal end portion of the knot tying device may have a slightly smaller diameter than the proximal end portion to facilitate the suture flow once the knot is developed and the device is retracted.

In various exemplary embodiments, the knot tying device may include a handle/buttons that allows the clinician to move/activate the device and sheath (when present) longitudinally (and also circularly), and the handle is sufficiently long and positioned sufficiently close to the instrument being used so that it does not interfere with operation of the instrument and the clinician does not need to struggle or push against tissues or trocars when the knot-tying device is extended or retracted while tying the knot.

In various exemplary embodiments, in order to accommodate instruments of various lengths, the knot tying device might have one or more of the following: expandable arms, folding arms, curling arms, telescoping arms, a telescoping shaft, an expandable shaft, an expandable bent/curved site, malleable arms, arms that adjust to the contour of the instrument and combinations thereof. The expandable portion might be, for example, telescoping, accordioned (similar to a drinking straw) and/or coiled.

In various exemplary embodiments, the knot tying device might allow for clockwise and/or counter-clockwise rotation.

In various exemplary embodiments, the knot tying device and or the sheath if present might have varying degrees of bend/angulation based upon need. The angulation might be pre-determined/fixed or adjustable.

In various exemplary embodiments, the knot-tying device might include a mechanism to prevent the device from moving or becoming loose/dislodged while the surgical instrument on which it is mounted is being used, or while it is deployed and a knot is being tied. The securing/anchoring might be activated/deactivated by a clinician based on ongoing needs and use. Examples of such securing/anchoring mechanisms may include but are not limited to the following types: toothed surfaces, hooks, hook-and-loop fastener (e.g., VELCRO®), securing lock, adhesive surface, ball and socket, click mechanism, peg-in-groove coupling, rail-in-groove, interference fit, ratchet/teeth, magnet, hook, tie, elastic band, magnet, electromagnet, screw/twist and combinations thereof.

It should be appreciated that although the knot tying device, that could include potentially a sheath 3000 and/or wire-like arm/handle 2300, may have a bend/angulation in its resting configuration (prior to being mounted on an instrument), in other exemplary embodiments the knot-tying device is straight in its resting configuration and acquires the bend/angulation only when deployed.

In various exemplary embodiments, the knot tying device might include a coil (or other configuration that could be deployed and would allow an easier construction of a knot) with a magnet/electromagnet rather than a bend/angulation at its tip. This variation might include a rotational motion to disengage the suture from the coil as the device is retracted and the knot is constructed.

In various exemplary embodiments, the knot-tying device can be used in a number of ways, including, for example:
using in a fixed position by simply deploying it (without rotating it);
using by deploying and rotating it (clockwise and/or counterclockwise);
rotating by rotating the arms/handles of the sheath, independent of the instrument on which it is mounted;
rotating by keeping the arms/handles of the sheath close to the rotational mechanism of the instrument, and rotating the mechanism together with the knot-tying device (rotating the instrument and the device together will have no detrimental effect);
rotating by rotating the entire instrument on which it is mounted; and
a combination of the above.

The knot-tying device could be (based on the preference of the operator):
used/activated in a fixed position by simply deploying it (without rotating it); used by deploying and rotating it (clockwise and/or counterclockwise); rotated by rotating the arms/handles of the device, independent of the instrument on which it is mounted; rotated by keeping the arms/handles of the device close to the rotational mechanism of the instrument, and rotating the mechanism together with the knot-tying device (the active end of the laparoscopic instrument is covered by the knot-tying device, and rotating the instrument and the device together will have no detrimental effect); rotated by rotating the entire instrument on which it is mounted; a combination of the above.

In exemplary embodiments, the knot tying device may involve magnetizing/electromagnetizing an entire laparoscopic/robotic instrument itself or otherwise a part or parts of the laparoscopic/robotic instrument while performing the tying of the knot, and removing the magnetization/electromagnetization once the maneuver is accomplished.

In exemplary embodiments, the knot tying device may apply a sealant or adhesive or other type of securing substance or device to the suture prior to making the knot, while making the knot and/or after making the knot. The securing substance may be, for example, glue, a biological product, degradable, non-biodegradable, or have any other suitable characteristic, and may result in application of heat or cold. The securing substance may be in drip, spray or any other suitable form.

The knot tying device may be an instrument by itself rather than a device that is placed on an instrument.

While in the foregoing specification a detailed description of a specific embodiment of the invention was set forth, it will be understood that many of the details herein given may be varied considerably by those skilled in the art without departing from the spirit and scope of the invention.

The invention claimed is:

1. A method of making a knot tying device assembly, comprising:
providing a surgical instrument comprising a proximal end portion and a distal end portion, the distal end portion of the surgical instrument configured to engage a suture; and
attaching a knot tying device to the surgical instrument, the knot tying device comprising a sheath, the sheath comprising:
a proximal end portion; and
a distal end portion that is elastically reconfigurable between a straightened configuration and a hook shaped configuration,
wherein the step of attaching comprises disposing the sheath over the surgical instrument so that the proximal end portion of the surgical instrument is disposed within the sheath,
wherein the position of the sheath on the surgical instrument is adjustable between an extended position in which the sheath extends beyond a distal tip of the surgical instrument and a retracted position in which the sheath is pulled back from the distal tip of the surgical instrument, and wherein the distal end portion is in the hook shaped configuration when the sheath is in the extended position and the distal end portion is in the straightened configuration when the sheath is in the retracted position, and
wherein the distal tip portion of the surgical instrument is operable to move the suture relative to the distal end portion of the sheath when the sheath is in the retracted position.

2. The method of claim 1, wherein the surgical instrument is a laparoscopic surgical instrument.

3. The method of claim 1, wherein the surgical instrument is of a type selected from the group consisting of: cannulas, trocars, scissors, graspers, forceps, hooks, probes, knot pushers, dissectors of all types, needles, needle holders, needle drivers, rigid scopes, trocar incision closure devices, catheters, harmonic scalpels, vessel sealing devices, energy delivery devices, irrigators, suctions, electric/hydraulic/pneumatic/sonic devices, retractors, and holders of the sheath.

4. The method of claim 1, wherein the knot tying device is reusable.

5. The method of claim 1, wherein the knot tying device is a single use device.

6. The method of claim 1, further comprising providing one or more additional knot tying devices, wherein the knot tying device and the one or more additional knot tying devices make up a set of knot tying devices, each knot tying device within the set is made up of two or more components.

7. The method of claim 6, wherein the two or more components of each knot tying device are interchangeable with corresponding two or more components of the other knot tying devices within the set.

8. The method of claim 6, wherein the two or more components are not interchangeable with corresponding two or more components of the other knot tying devices within the set.

9. A method of making a kit for knot tying, the method comprising making a knot tying device assembly in accordance with claim 1 and providing an instruction manual.

10. A method of making a knot tying device assembly, comprising:
   providing a surgical instrument comprising a proximal end portion and a distal end portion, the distal end portion of the surgical instrument configured to engage a suture; and
   attaching a knot tying device to the surgical instrument, the knot tying device comprising:
      a main body;
      a proximal end portion; and
      a distal end portion that is elastically reconfigurable between a straightened configuration and a hook shaped configuration,
   wherein the step of attaching comprises movably fixing the main body of the knot tying device to the surgical instrument so that the knot tying device and the surgical instrument form a unitary structure and the proximal end portion of the surgical instrument is disposed within the main body,
   wherein the position of the main body on the surgical instrument is adjustable between an extended position in which the main body extends beyond a distal tip of the surgical instrument and a retracted position in which the main body is pulled back from the distal tip of the surgical instrument, and wherein the distal end portion is in the hook shaped configuration when the main body is in the extended position and the distal end portion is in the straightened configuration when the main body is in the retracted position, and
   wherein the distal tip portion of the surgical instrument is operable to move the suture relative to the distal end portion of the main body when the main body is in the retracted position.

11. A method of making a knot tying device, comprising:
   (A) providing a surgical instrument comprising a proximal end portion and a distal end portion, the distal end portion of the surgical instrument configured to engage a suture;
   (B) attaching a knot tying device to the surgical instrument, the knot tying device comprising a sheath, the sheath comprising:
      i) a proximal end portion; and
      ii) a distal end portion that is elastically reconfigurable between a straightened configuration and a hook shaped configuration,
   wherein the step of attaching comprises disposing the sheath over the surgical instrument so that the proximal end portion of the surgical instrument is disposed within the sheath;
   (C) disposing one or more magnets on at least one of the surgical instrument or the sheath,
   wherein the position of the sheath on the surgical instrument is adjustable between an extended position in which the sheath extends beyond a distal tip of the surgical instrument and a retracted position in which the sheath is pulled back from the distal tip of the surgical instrument, and wherein the distal end portion is in the hook shaped configuration when the sheath is in the extended position and the distal end portion is in the straightened configuration when the sheath is in the retracted position, and
   wherein the distal tip portion of the surgical instrument is operable to move the suture relative to the distal end portion of the sheath when the sheath is in the retracted position.

12. The method of claim 11, wherein the one or more magnets are disposed on the sheath.

13. The method of claim 12, further comprising the step of providing the knot tying device with an activation mechanism that moves the one or more magnets or the sheath with at least one of linear or rotational movement relative to the surgical instrument.

14. The method of claim 13, wherein the activation mechanism is of a type selected from the group consisting of: hydraulic, pneumatic, mechanical, potential energy, kinetic energy, ultrasonic, sonic, electrical, magnetic, electromagnetic, and combinations thereof.

15. The method of claim 11, wherein the one or more magnets are disposed on the surgical instrument.

16. The method of claim 11, wherein at least a portion of the sheath is made of an elastic material.

17. The method of claim 11, wherein at least a portion of the sheath is made of a material selected from the group consisting of: metal, magnetic material, electromagnetic material, polyethylene, silicone rubber, natural rubber, PVC, polyurethane, polypropylene, polyester, polyether ether ketone, polyphenylsulfone, nylon, polytetrafluoroethylene, resins and combinations thereof.

18. A method of making a kit for knot tying, the method comprising making a knot tying device in accordance with claim 11 and providing an instruction manual.

19. A method of making a knot, comprising:
   adjusting a position of a sheath disposed on a surgical instrument between an extended position in which the sheath extends beyond a distal tip of the surgical instrument and a retracted position in which the sheath is pulled back from the distal tip of the surgical instrument,
      wherein a proximal end portion of the surgical instrument is disposed within the sheath, a distal end portion of the surgical instrument configured to engage a suture, a distal end portion of the sheath has a hook shaped configuration when the sheath is in the extended position and a distal end portion of the sheath has a straightened configuration when the sheath is in the retracted position, grasping the suture with the distal end portion of the sheath when the sheath is in the extended position; and moving the suture with the distal tip portion of the surgical instrument relative to the distal end portion of the sheath when the sheath is in the retracted position.

\* \* \* \* \*